(12) United States Patent
Matteo et al.

(10) Patent No.: US 9,457,200 B2
(45) Date of Patent: ***Oct. 4, 2016

(54) SYSTEMS AND METHODS OF ADJUSTING A ROTATING GANTRY SYSTEM

(71) Applicant: ProNova Solutions, LLC, Knoxville, TN (US)

(72) Inventors: Joseph C. Matteo, Walland, TN (US); Jonathan Huber, Knoxville, TN (US); Peter Hansen, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/598,710

(22) Filed: Jan. 16, 2015

(65) Prior Publication Data

US 2015/0126801 A1 May 7, 2015

Related U.S. Application Data

(63) Continuation-in-part of application No. 14/064,732, filed on Oct. 28, 2013, now Pat. No. 8,963,108.

(60) Provisional application No. 61/719,129, filed on Oct. 26, 2012, provisional application No. 61/880,605, filed on Sep. 20, 2013.

(51) Int. Cl.
*G21K 5/04* (2006.01)
*A61N 5/10* (2006.01)
*F16C 19/54* (2006.01)

(52) U.S. Cl.
CPC .............. *A61N 5/1081* (2013.01); *F16C 19/54* (2013.01); *A61N 2005/1087* (2013.01); *Y10T 29/49826* (2015.01)

(58) Field of Classification Search
USPC ........... 250/396 R, 397, 492.1, 492.3; 600/1; 315/500, 501, 502, 503, 504, 505, 506, 315/507
See application file for complete search history.

(56) References Cited

U.S. PATENT DOCUMENTS 7,372,053 B2   5/2008   Yamashita et al.
7,381,979 B2   6/2008   Yamashita et al.
(Continued)

FOREIGN PATENT DOCUMENTS

WO   WO2011/036254   3/2011

OTHER PUBLICATIONS

Patent Cooperation Treaty; Int'l Search Report for App'l No. PCT/US2013/067098; Date of mailing May 14, 2014; form PCT/ISA/237.

*Primary Examiner* — Nicole Ippolito
(74) *Attorney, Agent, or Firm* — Pitts & Lake, P.C.

(57) ABSTRACT

A gantry wheel adjustment system and method to adjust a gantry wheel of a proton treatment system, including an estimation unit to estimate a bearing adjustment value for each of the adjustable bearings based on a stiffness parameter of each adjustable bearing, the stiffness parameter being a function of a force applied at each adjustable bearing and a deflection of the gantry wheel associated with the force applied at each adjustable bearing, the bearing adjustment value corresponding to a nominal position value for each adjustable bearing to compensate for gantry wheel flexing when the gantry wheel is rotated from a first angular position to a second angular position, the adjustable bearings being configured to support the gantry wheel on the bearing surface and maintain the proton beam at the isocenter of the gantry wheel during gantry wheel rotation.

20 Claims, 22 Drawing Sheets

(56) References Cited

U.S. PATENT DOCUMENTS

| | | |
|---|---|---|
| 7,961,844 B2 | 6/2011 | Takeda et al. |
| 8,963,108 B2 * | 2/2015 | Matteo .............. A61N 5/1081 250/396 R |
| 2007/0284548 A1 | 12/2007 | Kaiser et al. |
| 2012/0224667 A1 | 9/2012 | Cheng et al. |

* cited by examiner

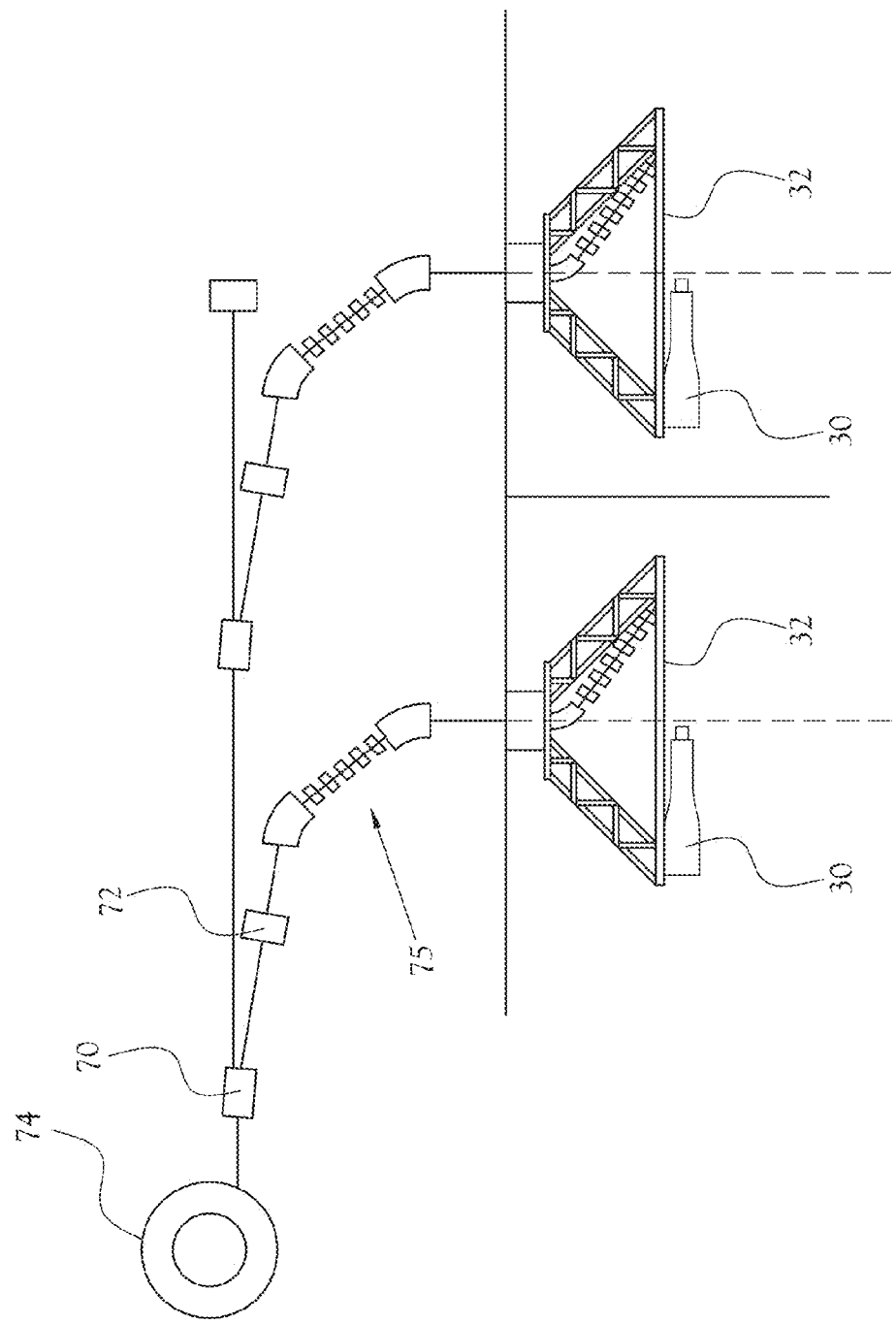

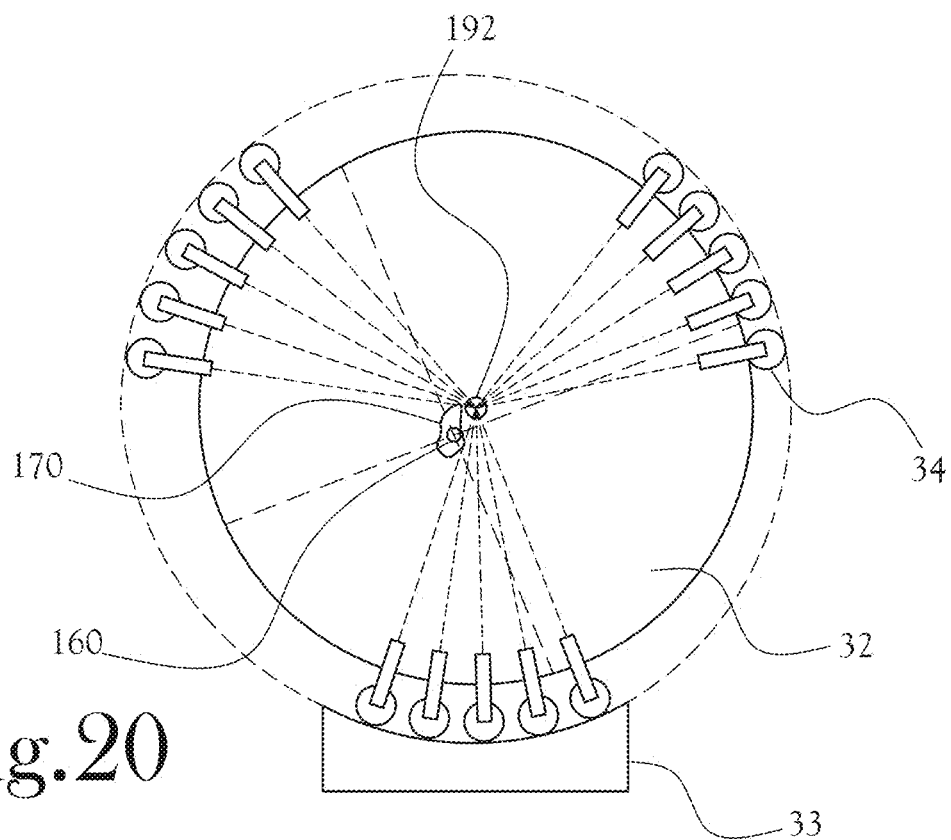
Fig.20
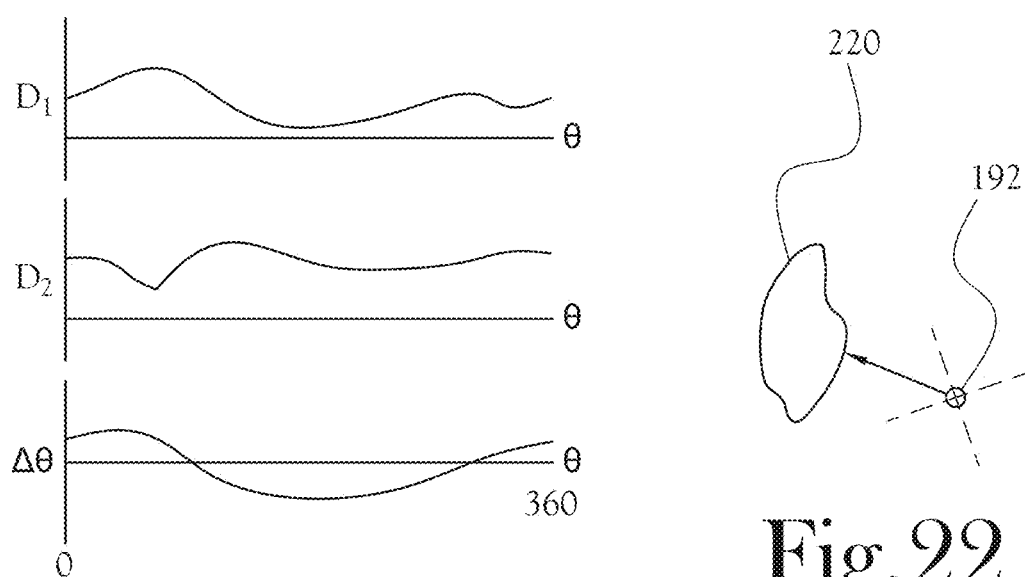
Fig.21
Fig.22

SYSTEMS AND METHODS OF ADJUSTING A ROTATING GANTRY SYSTEM

CROSS-REFERENCE TO RELATED APPLICATIONS

This application is a Continuation-In-Part of U.S. application Ser. No. 14/064,732, filed on Oct. 28, 2013, which claims priority from U.S. Provisional Application Nos. 61/719,129, filed on Oct. 26, 2012, and 61/880,605, filed on Sep. 20, 2013, the disclosures of which are incorporated by reference herein.

FIELD OF INVENTION

The present general inventive concept relates to a rotating gantry system, and more particularly, to systems and methods of adjusting a rotating gantry system to maintain alignment of ae proton delivery mechanism with respect to the gantry's axis of rotation for proton therapy.

BACKGROUND

Proton Therapy (PT) is a cancer treatment technology that uses high energy protons to penetrate a patient's body and deposit energy into treatment areas such as cancerous tumors. PT systems commonly implement a rotating gantry wheel that directs the proton beam to the patient from any angle between zero and 360 degrees. This allows the physician to design a treatment plan that attacks cancerous tumors from different angles and reduces radiation damage to critical organs and/or healthy tissue.

One of the challenges facing PT systems is to maintain proper alignment between the proton delivery nozzle and the isocenter of the rotating gantry system when the gantry is rotated to different treatment angles. For example, it is desirable to maintain accuracy of the proton beam to the gantry center in order to accurately focus the proton beam to a targeted area of interest. Due to inherent fabrication tolerances and the extreme size and weight of the gantry apparatus and its various components, the structure can deflect when rotated at different angles, allowing the system's center to drift above the target accuracy.

It is known to move the patient bed to compensate for subtle drifts in the system at different angles of rotation. However, moving the patient to compensate for beam misalignment can become quite time consuming and complicated, especially if the treatment plan requires more than one application angle for each patient. Therefore, it would be desirable to align the gantry apparatus itself in anticipation of the deviances that occur through rotation of the gantry apparatus.

Another challenge facing PT systems is the time it takes to construct and implement a working system. For example, it typically takes about 6 months to build a gantry on site and an additional 12 months to commission the equipment. This lengthy build time is largely associated with the size of the magnets required to direct protons through the gantry and the related beam accuracy demands.

BRIEF SUMMARY

The present general inventive concept provides various embodiments of a proton treatment gantry apparatus, a proton treatment gantry system, and a method of operating and/or configuring the proton treatment gantry apparatus and system.

Additional features and embodiments of the present general inventive concept will be set forth in part in the description which follows, and, in part, will be obvious from the description, or may be learned by practice of the present general inventive concept.

Example embodiments of the present general inventive concept may be achieved by providing a gantry apparatus for a proton treatment system, including a proton beam nozzle to emit a proton beam to a targeted region of a patient, a gantry wheel to support the proton beam nozzle to direct the proton beam to an isocenter of the gantry wheel corresponding to a center of the targeted region, a plurality of adjustable bearings incrementally spaced apart along an outer diametrical surface of the gantry wheel, and a bearing surface to support a portion of the adjustable bearings such that when the wheel is rotated from a first angular position to a second angular position, at least a portion of the bearings contact the bearing surface to raise or lower the gantry wheel to realign the proton beam to the center of the targeted region.

The adjustable bearings may respectively include one or more bearing rollers, and an adjustable member coupled to the one or more bearing rollers and provided adjacent to a circumferential surface of the gantry wheel such that the one or more bearing rollers are selectively movable relative to the circumferential surface.

The adjustable member may be configured to slidably reciprocate radially with respect to the circumferential surface.

The adjustable member may further include one or more locking members provided to the adjustable member to fix the adjustable member in a selected position.

The adjustable bearings may further respectively include an adjusting member to drive movement of the adjustable member.

Example embodiments of the present general inventive concept may also be achieved by providing a method of making a gantry wheel apparatus for a proton treatment system, the method including establishing an isocenter of a gantry wheel, mounting a plurality of adjustable bearings at incrementally spaced locations along an outer diametrical surface of the gantry wheel, setting the gantry wheel on a bearing surface such that a portion of the bearings contact the bearing surface, adjusting the adjustable bearings such that when the gantry wheel is rotated, the isocenter does not shift, and machining a reference surface to the gantry wheel while the wheel is rotating.

Example embodiments of the present general inventive concept may also be achieved by providing a gantry apparatus for a proton treatment system, including a proton beam nozzle to emit a proton beam to a targeted region of a patient, a gantry wheel having an eccentric outer surface, the proton beam nozzle being mountable to the gantry wheel to direct the proton beam to an isocenter of the gantry wheel corresponding to a center of the targeted region, and a bearing surface to support the gantry wheel such that when the gantry wheel rotates, the bearing surface contacts the eccentric outer surface to raise or lower the gantry wheel to maintain proton beam alignment to the center of the targeted region.

Example embodiments of the present general inventive concept may also be achieved by providing a method of aligning a gantry apparatus for a proton treatment system, the method including estimating an isocenter and center-of-rotation of a gantry, modeling changes in nozzle-trajectory in response to predetermined changes in hydraulic actuator displacement and rotation angle, determining actuator displacements and correction to rotations angle that minimize a nozzle-trajectory error at each of the rotation angles, and adjusting cam-followers according to the determined actuator displacements and correction to rotations angles.

The method may further include identifying position and orientation errors of the nozzle-trajectory at various rotation angles of the gantry to estimate the isocenter and center-of-rotation.

The nozzle-trajectory may be determined by measuring a plurality of points on the nozzle with a laser ranging system.

The modeling may further include determining sensitivity functions corresponding to the modeled changes, the sensitivity functions forming a linearized model of the gantry.

The correction to rotations angles may be stored in a look-up table.

The determining of the actuator displacements and correction to rotations angles selectively may include a smooth alignment corresponding to a single center-of-rotation, or an optimized alignment corresponding to a path that limits a rate-of-change of the center-of-rotation as the gantry rotates.

The adjusting of the cam-followers may include raising the gantry off of the cam-followers with hydraulic actuators, moving the cam-followers to obtain maximum clearance, repositioning the gantry with the hydraulic actuators, adjusting the cam-followers to support the gantry, and retracting the hydraulic actuators.

The method may further include re-estimating the isocenter and center-of-rotation of the gantry in response to the cam-followers being adjusted.

Example embodiments of the present general inventive concept may also be achieved by providing a system to adjust a gantry apparatus of a proton treatment system, including a gantry to carry a proton beam nozzle, the proton beam nozzle being configured to emit a proton beam to an isocenter of the gantry, one or more adjustable members spaced apart about a circumference of the gantry to rotatably support the gantry on a supporting surface, one or more displacement members to displace the gantry from the supporting surface, and a controller to model changes in nozzle-trajectory as the gantry rotates on the supporting surface, and to determine a corrective displacement of the gantry at various rotation angles to minimize a nozzle-trajectory error at each of the rotation angles.

The one or more adjustable members may be actuated to be automatically controlled.

The gantry center of rotation may be the same point in space as the center of the system's sphere of confusion.

An actuation may be provided on the gantry to move the nozzle trajectory to the isocenter.

The one or more adjustable members may be actuated to be automatically controlled via feedback of an external measurement, i.e. vision system or laser interferometer.

Example embodiments of the present general inventive concept may also be achieved by providing a proton treatment system including a particle accelerator to generate a proton beam, a proton beam nozzle to emit the proton beam to a targeted region of a patient, a beamline path to direct the proton beam from the particle accelerator to the proton beam nozzle, a gantry wheel to support the proton beam nozzle to direct the proton beam to an isocenter of the gantry wheel corresponding to a center of the targeted region, a plurality of adjustable bearings incrementally spaced apart along an outer diametrical surface of the gantry wheel, and a bearing surface to support a portion of the adjustable bearings such that when the wheel is rotated from a first angular position to a second angular position, at least a portion of the bearings contact the bearing surface to raise or lower the gantry wheel to realign the proton beam to the center of the targeted region.

Example embodiments of the present general inventive concept may also be achieved by providing a gantry wheel adjustment system and method to adjust a gantry wheel of a proton treatment system, including an estimation unit to estimate a bearing adjustment value for each of the adjustable bearings based on a stiffness parameter of each adjustable bearing, the stiffness parameter being a function of a force applied at each adjustable bearing and a deflection of the gantry wheel associated with the force applied at each adjustable bearing, the bearing adjustment value corresponding to a nominal position value for each adjustable bearing to compensate for gantry wheel flexing when the gantry wheel is rotated from a first angular position to a second angular position, the adjustable bearings being configured to support the gantry wheel on the bearing surface and maintain the proton beam at the isocenter of the gantry wheel during gantry wheel rotation.

Example embodiments of the present general inventive concept may also be achieved by providing a gantry wheel adjustment system to adjust a gantry wheel of a proton treatment system, the proton treatment system including a proton beam nozzle to direct a proton beam to an isocenter of the gantry wheel, a plurality of adjustable bearings incrementally spaced apart along an outer diametrical surface of the gantry wheel, and a bearing surface to receive a portion of the adjustable bearings such that the gantry wheel is supported on the bearing surface by the portion of adjustable bearings received thereon, the gantry wheel adjustment system including an estimation unit to estimate a bearing adjustment value for each of the adjustable bearings based on a stiffness parameter of each adjustable bearing, the stiffness parameter being a function of a force applied at each adjustable bearing and a deflection of the gantry wheel associated with the force applied at each adjustable bearing, the bearing adjustment value corresponding to a nominal position value for each adjustable bearing to compensate for gantry wheel flexing when the gantry wheel is rotated from a first angular position to a second angular position, the adjustable bearings being configured to support the gantry wheel on the bearing surface and maintain the proton beam at the isocenter of the gantry wheel during gantry wheel rotation.

The gantry apparatus may include a proton beam nozzle to emit a proton beam to a targeted region of a patient, a gantry wheel to support the proton beam nozzle to direct the proton beam to an isocenter of the gantry wheel corresponding to a center of the targeted region, a plurality of adjustable bearings incrementally spaced apart along an outer diametrical surface of the gantry wheel, a bearing surface to support a portion of the adjustable bearings such that when the gantry wheel is rotated from a first angular position to a second angular position, at least a portion of the bearings contact the bearing surface to raise or lower the gantry wheel to realign the proton beam to the center of the targeted region, a deflection measuring unit to measure a deflection value of the gantry wheel at each adjustable bearing according to a force applied to each of the adjustable bearings, and a nominal positioning unit to determine a nominal value of gantry wheel compression at each adjustable bearing according to the deflection value.

The gantry apparatus may further include a position determination unit to determine initial positions for each of the adjustable bearings, the initial positions being achieved by extending the respective adjustable bearings to a corresponding length.

The gantry apparatus may further include a linear approximation unit to approximate gantry wheel flexing at each adjustable bearing position.

The linear approximation unit may approximate the gantry wheel flexing for a plurality of the adjustable bearings that will be simultaneously contacting the bearing surface.

The linear approximation unit may approximate the gantry wheel flexing according to the sum of forces acting on the adjustable bearings contacting the bearing surface by the bearing surface being equal to the weight of the gantry wheel.

The linear approximation unit may approximate the gantry wheel flexing for five or six adjustable bearings simultaneously contacting the bearing surface at five degree incremental spacing.

The linear approximation unit may determine force balance equations in x and y directions for each of adjustable bearings contacting the bearing surface.

The linear approximation unit may determine residual errors according to force balance equations determined for configurations including both five and six adjustable bearings contacting the bearing surface.

Example embodiments of the present general inventive concept may also be achieved by providing a method of aligning a gantry apparatus for a proton treatment system, the method including measuring a weight of a gantry wheel on a bearing surface, the gantry wheel being configured to rotate and being supported on the bearing surface by a plurality of adjustable bearings, measuring a corresponding deflection of the gantry wheel according to a force respectively applied to each of the adjustable bearings, and determining a nominal operation point of the gantry wheel according to the measured weight and deflections.

The method may further include determining initial positions for each of the adjustable bearings, the initial positions being achieved by extending the respective adjustable bearings to a corresponding length.

The method may further include approximating, by a linear approximation unit, gantry wheel flexing at each adjustable bearing position at the nominal operation point.

The linear approximation unit may approximate the gantry wheel flexing for a plurality of the adjustable bearings that will be simultaneously contacting the bearing surface.

The linear approximation unit may approximate the gantry wheel flexing according to the sum of forces acting on the adjustable bearings contacting the bearing surface by the bearing surface being equal to the weight of the gantry wheel.

The linear approximation unit may approximate the gantry wheel flexing for five or six adjustable bearings simultaneously contacting the bearing surface at five degree incremental spacing.

The linear approximation unit may determine force balance equations in x and y directions for each of adjustable bearings contacting the bearing surface.

The linear approximation unit may determine residual errors according to force balance equations determined for configurations including both five and six adjustable bearings contacting the bearing surface.

Example embodiments of the present general inventive concept may also be achieved by providing a method of aligning a gantry apparatus for a proton treatment system, the method including establishing an isocenter of a gantry wheel, rotating the gantry wheel such that a proton beam nozzle provided to the gantry wheel is at a predetermined position, adjusting a plurality of adjustable bearings provided to the gantry wheel and that are interfacing with a support surface until a projection from the proton beam nozzle is within a predetermined tolerance from both an axis of the gantry wheel and the isocenter, determining a primary adjustment value as a distance between the projection from the proton beam nozzle and the isocenter after adjustment at the predetermined position, rotating the gantry wheel a predetermined number of degrees and adjusting the interfacing adjustable bearings until the primary adjustment value is reached between the projection from the proton beam nozzle and the isocenter at each subsequent gantry wheel position, and repeating the rotation and adjustment until a full 360 degrees of rotation has been reached.

The predetermined position of the proton beam nozzle may be a 9 o'clock position relative to the gantry wheel.

Example embodiments of the present general inventive concept may also be achieved by providing a gantry wheel adjustment system to adjust a gantry wheel of a proton treatment system, the proton treatment system comprising a proton beam nozzle to direct a proton beam to an isocenter of the gantry wheel, a plurality of adjustable bearings incrementally spaced apart along an outer diametrical surface of the gantry wheel, and a bearing surface to receive a portion of the adjustable bearings such that the gantry wheel is supported on the bearing surface by the portion of adjustable bearings received thereon, the gantry wheel adjustment system including a rotation controller to rotate the gantry wheel such that the proton beam nozzle is at a predetermined position, a position detector to detect, during and/or after an adjusting a plurality of adjustable bearings provided to the gantry wheel and that are interfacing with a support surface, when a projection from the proton beam nozzle is within a predetermined tolerance from both an axis of the gantry wheel and the isocenter, and a primary adjustment value determination unit to determine a primary adjustment value as a distance between the projection from the proton beam nozzle and the isocenter after adjustment at the predetermined position, wherein the rotation controller rotates the gantry wheel a predetermined number of degrees such that the interfacing adjustable bearings may be adjusted until the primary adjustment value is reached between the projection from the proton beam nozzle and the isocenter at each subsequent gantry wheel position, and wherein the rotation and adjustment are repeated until a full 360 degrees of rotation of the gantry wheel has been reached.

Other features and embodiments of the present general inventive concept may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 7 is a graphic illustration of a proton therapy system configured in accordance with an example embodiment of the present general inventive concept;

FIG. 20 illustrates a smooth gantry alignment of an embodiment of the present general inventive concept;

FIG. 21 illustrates graphs indicating actuator displacements and gantry-angle-correction to compensate for flexing, as a function of gantry rotation angle, according to an embodiment of the present general inventive concept;

FIG. 22 illustrates the path of ideal center-of-rotation as being offset from the center-of-gantry point according to an embodiment of the present general inventive concept;

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of any processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
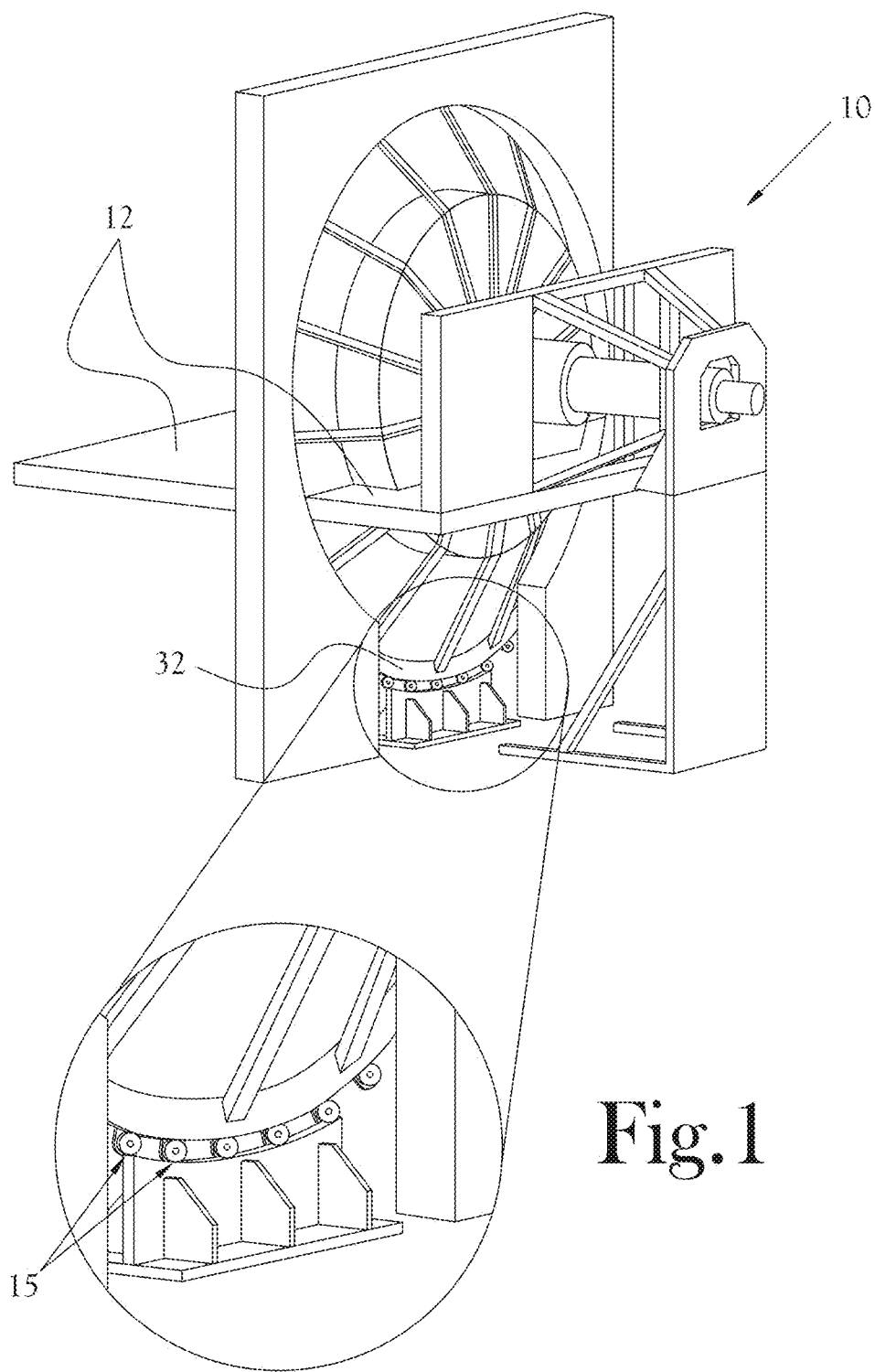
FIG. 1 is a graphic illustration of a gantry system configured in accordance with an example embodiment of the present general inventive concept.

Various example embodiments of the present general inventive concept, as described herein, provide FIG. 1 is a graphic illustration of a gantry system 10 configured in accordance with an example embodiment of the present general inventive concept. In proton therapy (PT) systems, it is common to use a gantry wheel 32 to rotate a proton nozzle (30 in FIG. 3) to direct a proton beam from any angle between zero and 360 degrees toward a patient lying on bed near the isocenter of the gantry wheel. As illustrated in FIG. 1, the gantry system 10 can include a mezzanine platform 12 for a technician to walk on, enabling a technician to access the magnets, nozzle, etc., for service. FIG. 1 also illustrates a cam follower/bearing surface arrangement 15 to align the wheel to a fixed isocenter, as described in greater detail below in connection with FIG. 3.

One of the challenges facing PT systems is to maintain proper alignment between the proton delivery nozzle and the isocenter of the rotating gantry system and targeted treatment area when the gantry is rotated to different treatment angles. For example, in most treatment plans it is desirable to maintain accuracy of the proton beam to the gantry center to accurately focus the proton beam to the center of a targeted area of interest, such as a tumor, in the patient. However, due to inherent fabrication tolerances and the extreme size and weight of the gantry apparatus, the structure can deflect when the wheel is rotated at different angles, allowing the system's center to drift above the target accuracy.

Another challenge facing PT systems is to make them smaller, lighter, and easier to fabricate, as the systems are quite large, weighty, and difficult to produce efficiently.

Figure 2:
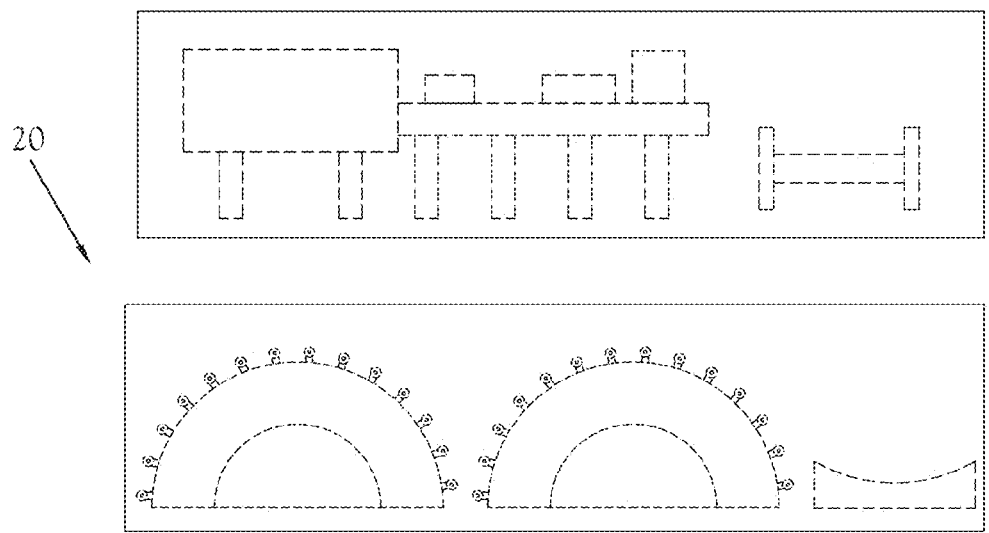
FIG. 2 is a graphic illustration of a rotating gantry system and associated magnet system packaged within a standard international shipping container for transport.

FIG. 2 is a graphic illustration of a rotating gantry system and associated magnet system packaged within standard international shipping containers 20 for transport. As discussed in greater detail below, embodiments of the present general inventive concept incorporate superconducting magnets that are smaller and lighter compared to conventional warm magnets. As a result, the gantry that houses those magnets can be equivalently smaller. These smaller gantry-magnets system can be assembled and aligned in a factory and then shipped intact, decreasing the overall build and commission time. It is possible for the complete gantry and frame to be shipped inside one container, and then the various parts may be unpacked, unfolded, etc., and assembled into a complete structure. Thus, the on-site build and commissioning time can be greatly reduced by completing as much as possible at the factory, and then shipping the system in large assemblies.

Figure 3:
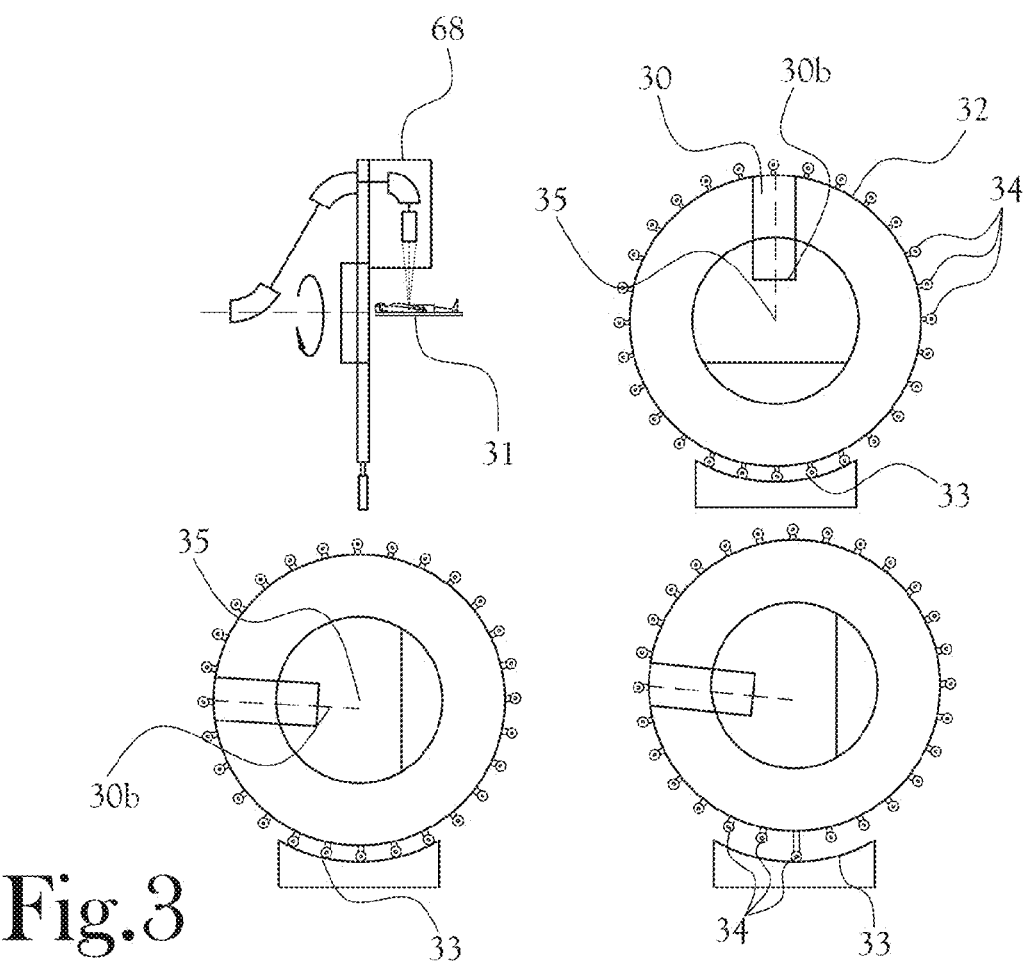
FIG. 3 is a diagram illustrating center-line drift of the gantry system with the gantry wheel rotated approximately 90 degrees.

FIG. 3 is a diagram illustrating the center-line drift and adjustment of the gantry system when the gantry wheel 32 is rotated approximately 90 degrees, according to an example embodiment of the present general inventive concept. Here, the proton beam nozzle is represented by reference number 30. The proton beam nozzle 30 projects a proton beam 30b to the isocenter of the wheel, which corresponds to the center 35 of the tumor when the patient is properly positioned on the bed 31.

Referring to the upper portion of FIG. 3, the nozzle 30 is oriented in the 12 o'clock position with the proton beam 30b directed downward to the target center. When the gantry wheel 32 is rotated 90 degrees counterclockwise, as illustrated in the bottom portion of FIG. 3, the proton beam 30b is directed off-target due to sagging of the structure. To compensate for this misalignment, instead of moving the patient as done in prior systems, a bearing surface 33, or cradle 33, can be provided to support the gantry wheel 32, and a plurality of bearings 34, or cam followers 34, can be provided on the outer diameter of the gantry wheel 32 to bear against the bearing surface 33. The bearings 34 can be selectively adjusted upward and downward (e.g., by turning threads) to raise and lower the entire gantry wheel 32 and nozzle apparatus, thus shifting the isocenter of the wheel to match the center of the targeted treatment area to compensate for wheel sag. It is understood that upward and downward are relative terms in this description, as the cam followers 34 may be adjusted to extend further from the diameter of the gantry wheel 32 to raise the gantry wheel 32 further from the bearing surface 33 when those particular cam followers 34 are contacting the bearing surface 33. Likewise, the cam followers 34 may be adjusted to be positioned closer to the diameter of the gantry wheel 32 to lower the gantry wheel 32 closer to the bearing surface 33 when those particular cam followers 34 are contacting the bearing surface 33. Since the center of the tumor does not move when the wheel rotates, adjusting the center of the wheel (and attached beam nozzle) relative to the center of the tumor at each angular position to compensate for wheel sag in each location is achieved.

Note that in the bottom right illustration of FIG. 3, only one of the bearings 34 (i.e., the middle bearing 34) is shown in the adjusted position for convenience of illustration. However, in practice, it is noted that each of the bearings 34 may be adjusted and brought into contact position with the bearing surface 33 such that when the wheel is rotated to any particular angle, the corresponding bearings 34 that are brought to interface with the bearing surface 33 will work against the outer diameter of the wheel 32 to align the proton beam with the isocenter at each angular location. For example, in the example embodiment illustrated in FIG. 3, there are twenty-four bearings spaced apart at 15 degree intervals along the outer diameter of the wheel 32, and the bearing surface 33 covers approximately 60 degrees of the wheel 32. Accordingly, in this embodiment, a maximum of five bearings 34 contact the bearing surface 33 at any one time. However, it will be appreciated by those skilled in the art that the present general inventive concept is not limited to any particular number of bearings 34, or length of bearing surface 33. More or less bearings 34 could be used at various angular spacing, and a longer or shorter bearing surface 33 could be used, without departing from the broader scope and content of the present general inventive concept. For example, some embodiments may use sixty bearings 34 spaced apart at 6 degree angles, and the bearing surface 34 may be sized to accommodate four bearings 34 at any one time.

One of the advantages of embodiments of the present general inventive concept is that it is possible to compensate for inherent deflection and manufacturing tolerances of the overall gantry system in order to maintain accuracy of the system, and improve patient care, with reduced manufacturing costs and shorter build and commission times for the equipment.

Figure 4:
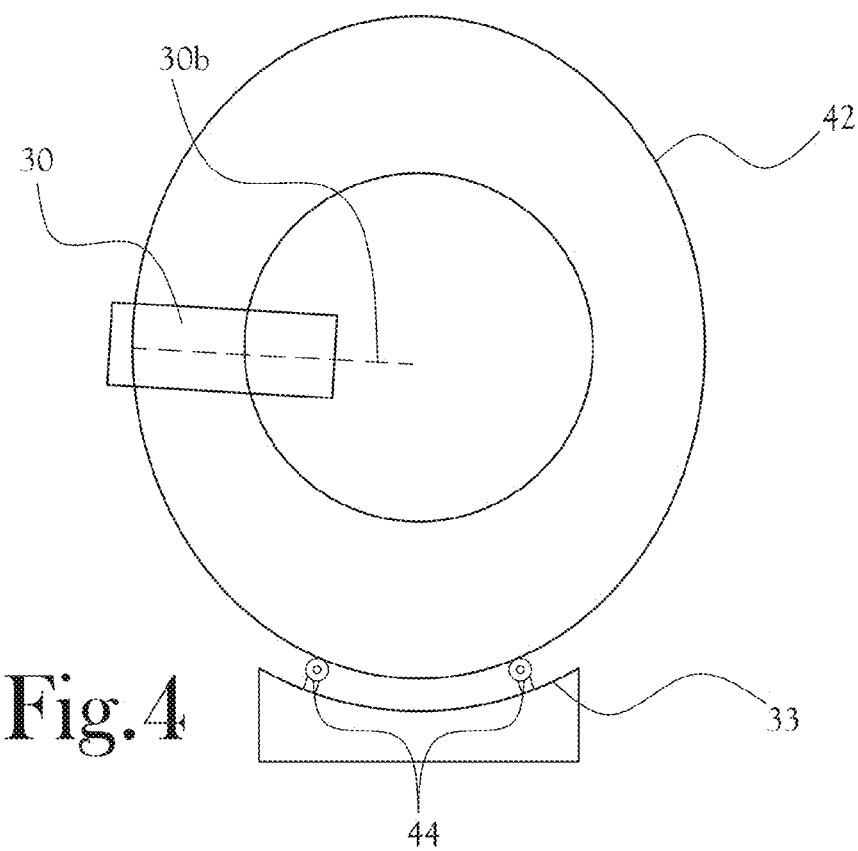
FIG. 4 is a diagram illustrating an eccentric gantry wheel configured in accordance with an example embodiment of the present general inventive concept.

FIG. 4 is a diagram illustrating an eccentric gantry wheel configured in accordance with another example embodiment of the present general inventive concept. In this embodiment, the cam followers are reversed and mounted on the bearing surface with adjustable or eccentric contact surfaces on the wheel. For example, a set of bearings 44 can be fixed to the bearing surface 33, and the gantry wheel 42 can be made eccentric, enabling the outer contact surface of the gantry wheel 42 to bear against the fixed bearings 44. When the gantry wheel 42 rotates among angular positions, the eccentric form of the gantry wheel 42, which is engaged against the bearing surface 33, serves to shift the isocenter of the wheel to match the stationary center of the targeted patient area, thus providing compensation for the high and low deflection that occurs at the various angular positions of the gantry wheel 42.

For example, referring to FIG. 4, when the eccentric gantry wheel 42 is at the 9 o'clock position, the configuration of the eccentric gantry wheel 42 (which is elongated vertically in this figure) raises the gantry wheel 42 with respect to the bearing surface 33 to compensate for greater deflection of the wheel, with results being the proton beam 30b remains aligned with the center of the tumor.

Figure 5:
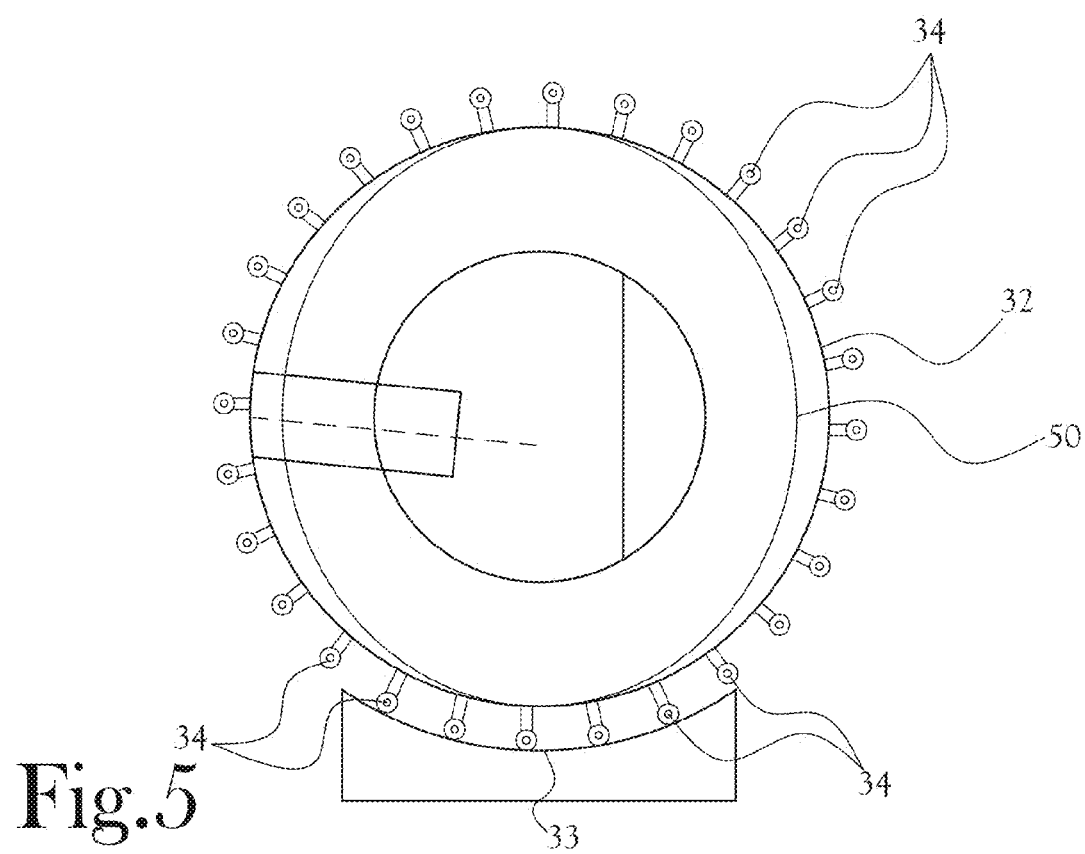
FIG. 5 is a diagram illustrating a circular gantry wheel with an eccentric machined edge configured in accordance with an example embodiment of the present general inventive concept.

FIG. 5 is a diagram illustrating a circular gantry wheel 32 with an eccentric machined edge 50 configured in accordance with an example embodiment of the present general inventive concept. This embodiment illustrates a calibration process in which the cam followers 34, as described above, are used to create concentricity between the beam line and the tumor center as the wheel 32 rotates through each angular position. In addition to field operation, this set-up can be used during a manufacturing process to calibrate wheel rotation using the cam followers 34, and then machining a concentric reference edge 50 with a stationary machine tool as the wheel rotates. The reference edge 50, which itself will be an eccentric shape, can then be used to run fixed bearings on to self-correct wheel deflection in the field, without having to use a plurality of cam following bearings as described above in the field. Thus, in addition to field use, the adjustable cam follower concept can be used in a manufacturing process to create concentric rotation, and then a machining step can be used to create a concentric reference surface for fixed cams to run on, effectively creating a self-correcting surface. In this way, using the cam followers to calibrate the wheel can also be the set-up process for manufacturing an eccentric reference surface.

Figure 6A:
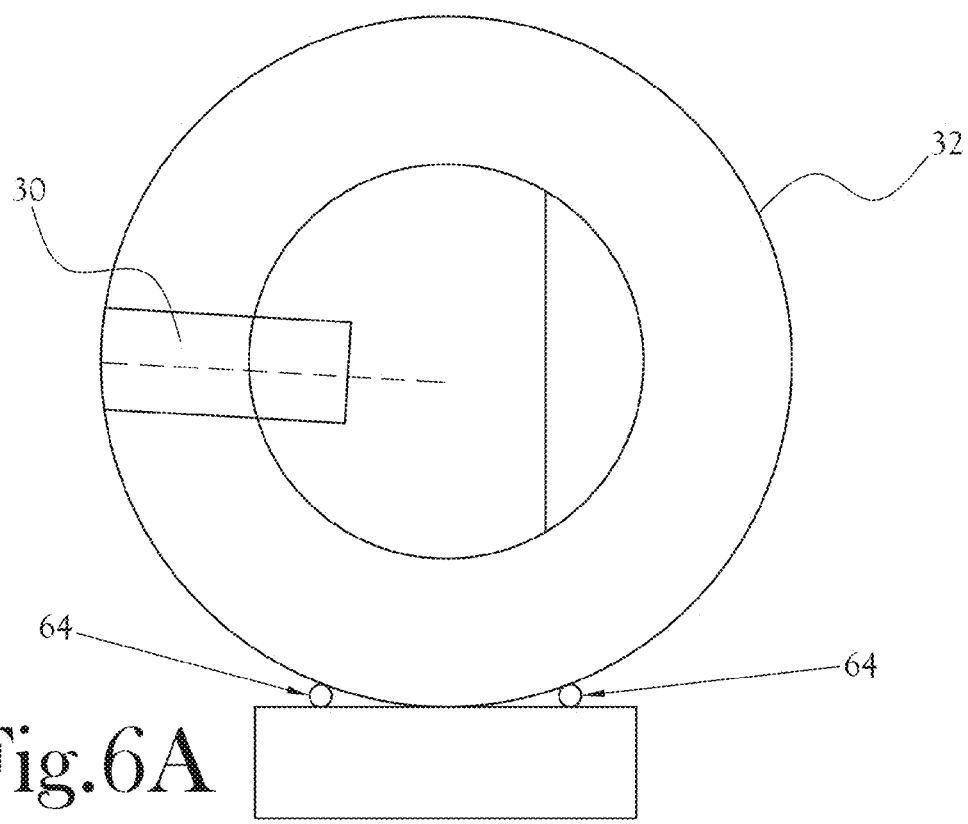
FIGS. 6A and 6B illustrate a gantry adjustment system configured in accordance with example embodiments of the present general inventive concept.
Figure 6B:
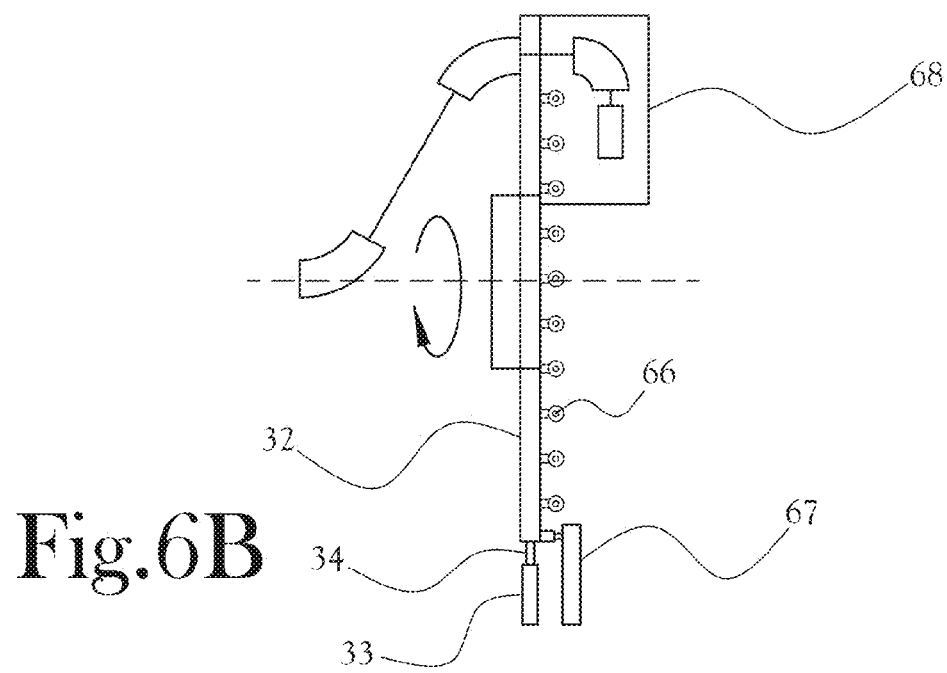

FIGS. 6A and 6B illustrate a gantry adjustment system configured in accordance with example embodiments of the present general inventive concept. Referring to FIG. 6A, it is possible to utilize actuated cam followers 64, or the cradle itself can be actuated, to correct for concentricity misalignment. Thus, the present general inventive concept contemplates active correction using cam followers 64, or the cradle itself, to move the wheel up and down, as the case may be, as the wheel rotates from angular position to angular position.

FIG. 6B illustrates that cam followers 66 can also be used to move the gantry wheel 32 in the z-axis, instead of, or in addition to, the cam followers 34 that move the gantry wheel 32 in the radial direction, to compensate for misalignment in the z-axis. One or more of the cam followers 66 that may be used to move the gantry wheel 32 in the z-axis (relative to the radial movement performed by the cam followers 34) may be in contact with a bearing surface 67, and may be adjustable in a similar manner to the cam followers 34. The bearing surface 67 which may be contacted by the one or more cam followers 66 may be fixed, or may also be adjustable to aid in the movement of the gantry wheel 32 in the relative z-axis.

In operation, embodiments of the present general inventive concept may provide adjustable multipoint contact bearings to enable precision concentricity of the nozzle, gantry, and treatment room within about 0.1 mm. Nozzle and gantry deflection up to about 5 mm can be removed, but the present general inventive concept is not limited to any particular range or degree of accuracy or adjustment.

Multipoint adjustment can be achieved by precision movement of the cam followers. Multipoint adjustment can also be facilitated by integrated lifting devices to precisely position the gantry wheel while the bearings are adjusted.

The gantry can include alignment and fiducial markers to assist in alignment of the magnets with respect to each other and the gantry. For example, in the factory, the magnetic fields can be aligned to the gantry devices, and then fiducial markers can be put on the gantry and the magnets so that when the wheel deflects, triangulation techniques using lasers can be used to pick up the locations of the markers to determine what correction to make to maintain alignment.

After an initial assembly at a gantry fabricator's facility, testing was performed for concept validation of the isocenter adjustment feature designed into the cam and cradle concept. During assembly, the gantry's home position was 9 o'clock (−90 degrees). The testing effort was placed on aligning the isocenter between the 11-7 o'clock rotational position (−170 through 40 degrees). The other cam plates were set via dead stopping gauge blocks against the cam plate and the adjustment block. The objectives of the testing were to determine if the cam follower concept is viable as a passive isocenter adjustment system, cursory evaluation of cam follower noise, cursory evaluation of cam follower vibration, and cursory evaluation of the cam follower alignment procedure. The intended outcome was to align the isocenter to ±0.5 mm, and obtain 360 degree isocenter data. The testing setup included a gantry without a nozzle, an active target bracket attached to the nozzle mount on the magnet frame, an API active target, and an API laser. Among the results of the testing were data regarding the isocenter offset, vibration, and the alignment procedure.

Regarding the isocenter offset, there was a distinct difference between the adjusted and gauge blocked cams. The adjusted cams typically resulted in 0.5 mm (1.0 mm max) offset whereas the gauge block cams were typically 1.0 mm (2.0 mm max) offset. This test focused solely on the y-axis alignment of the isocenter. As a result the dy offset range spanned ~0.4 mm. This is low compared to the dx and dz offset range of ~1 mm and ~1.2 mm, respectively. The isocenter variation along the y-axis for the aligned cams was 14% of the blocked, whereas the x- and z-axis were 50% and 43%, respectively. The resultant isocenter offset of the adjusted cams was 37% of the blocked type. Regarding the vibration results, the interface of the cradle race to the cam created a low vibration. No decibel recording was made, but the noise was generally quiet. A low frequency vibration was audible on cam contact. Regarding the alignment procedure results, the aligning of the cams does take some time. 22 cams at ±0.5 mm was done in three days, which places the first benchmark at 72 cams at ±0.5 mm in approximately 10 days. The lifting mechanism, tight spaces, and iteration were significant contributors to the time.

Conclusions from the results were that the preliminary adjustment of the cams demonstrated that ±0.5 mm isocenter offset is feasible. One complication may come from the x-axis offset. With the system as tested, the correction takes into account both the x- and y-axis. Hence, at a given position the y-axis may not be set to 0.0 because of the impact to the x-axis at other rotational positions. This effect will be examined further in later experimentation.

Referring back to FIGS. 3 and 6B, in various example embodiments of the general inventive concept the inventive gantry design may include an achromat 68 that may be mounted on only one side of the gantry wheel 32. Accordingly, when a technician walks on the mezzanine floor 12 (FIG. 1), the technician has ready access to the magnets for service or replacement. The design also allows for quick release of the achromat and hoses from the beamline and cooling system, simplifying magnet replacement and/or service.

FIG. 7 is a graphic illustration of a proton therapy system configured in accordance with an example embodiment of the present general inventive concept. The example embodiment of the proton therapy system of FIG. 7 includes two gantry wheels 32, each provided with a nozzle 30 and respective magnets 70, degraders 72, and energy selection systems 75, in which protons are fed to the nozzles 30 from a single cyclotron 74 along a beamline path.

Figure 8:
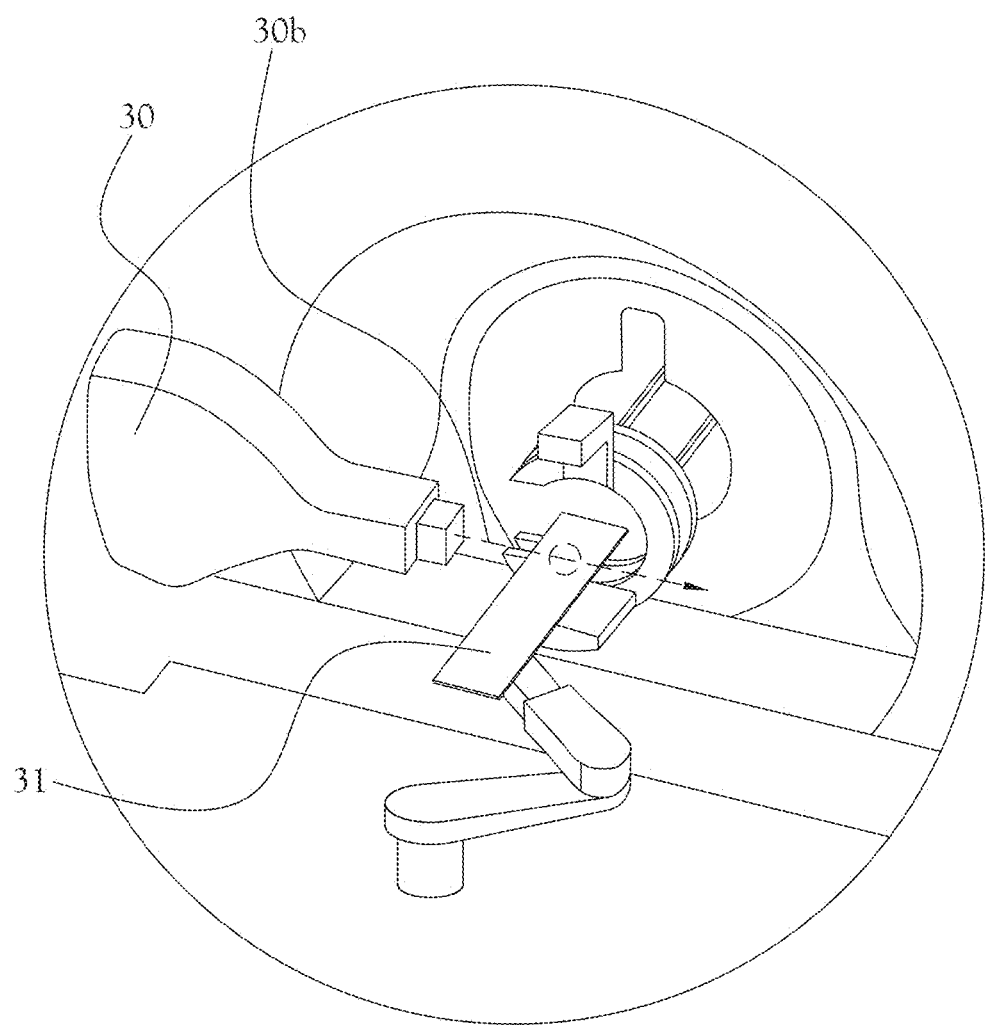
FIG. 8 a graphic illustration of a proton therapy system and environment configured in accordance with an example embodiment of the present general inventive concept.

FIG. 8 a graphic illustration of a proton therapy system and environment configured in accordance with an example embodiment of the present general inventive concept.

Various embodiments of the present general inventive concept provide a gantry wheel 32 that is supported by 5-6 cam-followers 34 contacting the bearing surface 33 at any given time, and the cam-followers 34 can be adjusted to compensate for flexing of the gantry system. There are several issues to be considered when determining how the cam-followers 34 should be adjusted to compensate for this flexing. For example, since the gantry wheel 32 is physically large and massive, it will be difficult for a technician to adjust the cam-followers 34 using a trial-and-error approach. Also, while modeling of the system may offer assistance in the adjustments, since no model is perfect, the additional effect of unmodeled flexing may be considered. It may be desirable that the adjustments to compensate for flexing provide smooth operation, as discontinuities may cause noise, vibration, and indeterminate positioning. Further, an automated process of adjusting the cam-followers may be desired to make the installation process efficient at new customer sites. In the various example embodiments described herein, the 5-6 cam-followers 34 that interact with the cradle 33 at any given time are interfacing with a 25 degree cradle 33. However, various other configurations are possible according to different examples of the present general inventive concept. For example, this concept may be applied in configurations such as a 1-2 cam-follower interface with a 5 degree cradle 33, a 36-37 cam-followers 34 interface with a 180 degree cradle 33, and so on. In various example embodiments, the cam-follower count may be driven by a 5 degree spacing from cam to cam. The cam spacing, cam loads, cradle 33 interface path, and gantry diameter are factors that may be used to determine the number of cams 34 interfacing with the cradle 33.

As illustrated in FIG. 8, the nozzle 30 trajectory should pass through the isocenter as the gantry wheel 32 rotates with the correct orientation, e.g., the orientation resulting from the proper adjustment of the cam-followers. At different points of rotation of the gantry wheel 32, some angle-dependent flexing of the gantry wheel 32 will occur, which may cause an error in the trajectory of the proton-beam from the nozzle. The nozzle-trajectory is the orientation of the axis along which the proton beam will emerge from the nozzle. Ideally, the nozzle-trajectory will pass through the isocenter with the correct orientation. The cam-followers 34 may be adjusted to compensate for as much flexing as possible. However, at the same time it may be desirable that the cam-followers 34 support the gantry as uniformly as possible. In various example embodiments of the present general inventive concept the portion of the cradle 33 that may be contacted by the cam-followers 34 may be configured to correspond to the circular shape of the gantry wheel 32, and therefore substantially perfect support may occur when the cam-followers 34 in contact with the cradle 33 form the same circular path. If the cam-followers 34 change the orientation of the gantry wheel 32 as it rotates, there may be some transition in which the gantry wheel 32 is not perfectly supported by the cradle. A significant transition may cause noise, vibration, and wear. If the transition is abrupt, the gantry wheel 32 may rock at some angles. At such a discontinuity, the positioning of the nozzle 30 may be indeterminate. Thus, it is desirable to compensate for as much flexing as possible with the smallest adjustments to the cam-followers 34.

Figure 9:
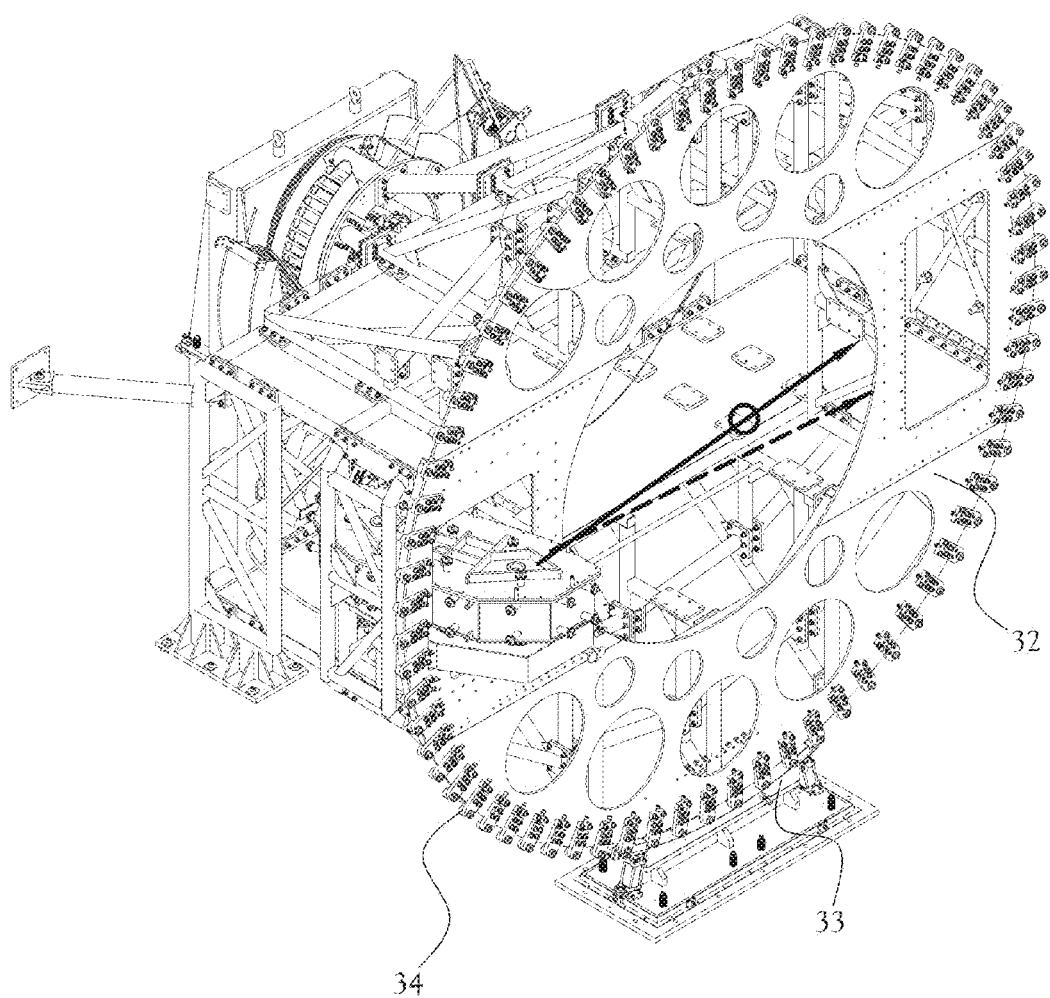
FIG. 9 illustrates various components of a gantry system according to an embodiment of the present general inventive concept.

FIG. 9 illustrates various components of a gantry system according to an embodiment of the present general inventive concept. The illustrated arrows extending from the nozzle 30 show an instance of gantry flexing similar to that illustrated in FIG. 2. As illustrated in FIG. 9, ideally the trajectory of the proton-beam would follow the solid arrow to the isocenter. However, as indicated by the broken arrow originating from the nozzle 30, sagging has caused the nozzle-trajectory to fall below the intended line. Flexing may translate and rotate the nozzle-trajectory, rather than there being just a sagging effect. Flexing depends on the rotation angle of the gantry, and, as no model is perfect, cannot be completely predicted by models. The gantry may be subject to hysteresis, as flexing is affected by the direction of the rotation. A repeatable method may be desirable to estimate the isocenter. Also, although the gantry may be stiff, a 1 mm isocenter is a very small target, so any flexing may be a concern.

Figure 10:
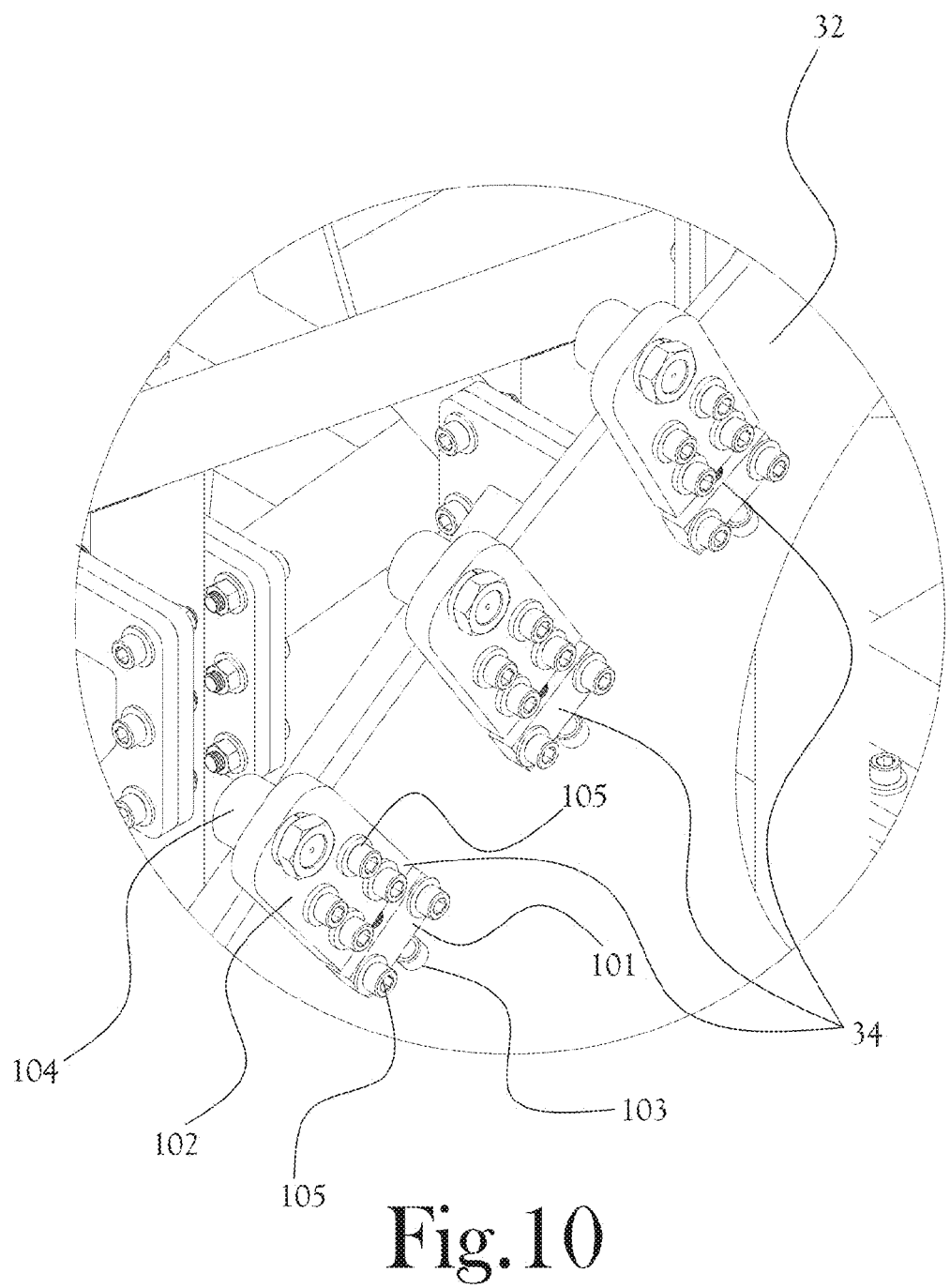
FIG. 10 illustrates a more detailed view of the cam-followers illustrated in FIG. 9 according to an embodiment of the present general inventive concept.

FIG. 10 illustrates a more detailed view of the cam-followers 34 illustrated in FIG. 9 according to an embodiment of the present general inventive concept. As previously described, the adjustable bearings/cam-followers 34 may be extended to move the gantry wheel 32 to correct for sagging. In various example embodiments, the cam-followers 34 may include fixed member 101 that may be coupled directly to the gantry wheel 32 near the outer diameter of the gantry wheel 32, an adjustable member 102 that may be extended from or retracted to the fixed member 101, and an adjusting member 103 to extend/retract the adjustable member 102. One or more bearing rollers 104 may be provided to each of the adjustable members 102 to contact the surface of the cradle 33 to support the gantry wheel 32. The bearing rollers 104 may be provided with an axle that is fixed to the adjustable member 102, so that the bearing rollers 104 may roll along the surface of the cradle 33 during contact with the cradle 33. According to various example embodiments, the bearing rollers 104 may have a diameter that is larger or smaller than, or substantially the same as, the width of the adjustable member 102 to which the bearing rollers 104 are respectively coupled. In the example embodiment illustrated in FIG. 10, the adjusting member 103 is configured as a threaded, screw-type adjuster that extends through fixed member 101 and into a corresponding threaded portion of the adjustable member 102, such that the turning of the adjusting member 103 causes the adjustable member 102, and therefore the bearing roller 104, to move away from or toward the outer diameter of the gantry wheel 32. The bearing rollers 104 may be coupled to the adjustable members 102 by conventional coupling members so as to provide sufficient support to the gantry wheel 32, as well as roll along the surface of the cradle 33. The fixed member 101 may be coupled to the gantry wheel 32 by conventional means, such as one or more of the illustrated bolts 105. The adjustable member 102 may also be fixed to a desired position by a conventional coupling means such as the illustrated bolts 105, which would be loosened by a technician before adjusting the position of the adjustable member 102 with the adjusting member 103, and then tightened upon the adjustable member 102 being moved to the desired position. The distal ends of the bolts 105 provided to the adjustable member 102 may be received in, for example, a corresponding groove provided in the gantry wheel 32 to guide the adjustable member 102 in a straight line when being extended or retracted, the threads of the bolts 105 interacting with a portion of the one or more receiving grooves. It is noted that the coupling means, i.e., the bolts 105, illustrated in FIG. 10 is merely one example of how the components of the bearings 34 may be fixed to the gantry wheel 32, and any of several other means known to those skilled in the art may be provided in other various examples of the present general inventive concept. Similarly, the bearing rollers 104 are merely one example of a bearing that contacts the cradle 33, as number of other adjustable configurations or devices such as, for example, ball bearings, may be provided in other various example embodiments. In other various example embodiments, the bearings 34 may not be provided with a rolling component, but rather may be a fixed point which interfaces with the cradle 33. For example, the bearings 34 may slide directly along the surface of the cradle 33 with the aid of lubrication, etc.

Figure 11:
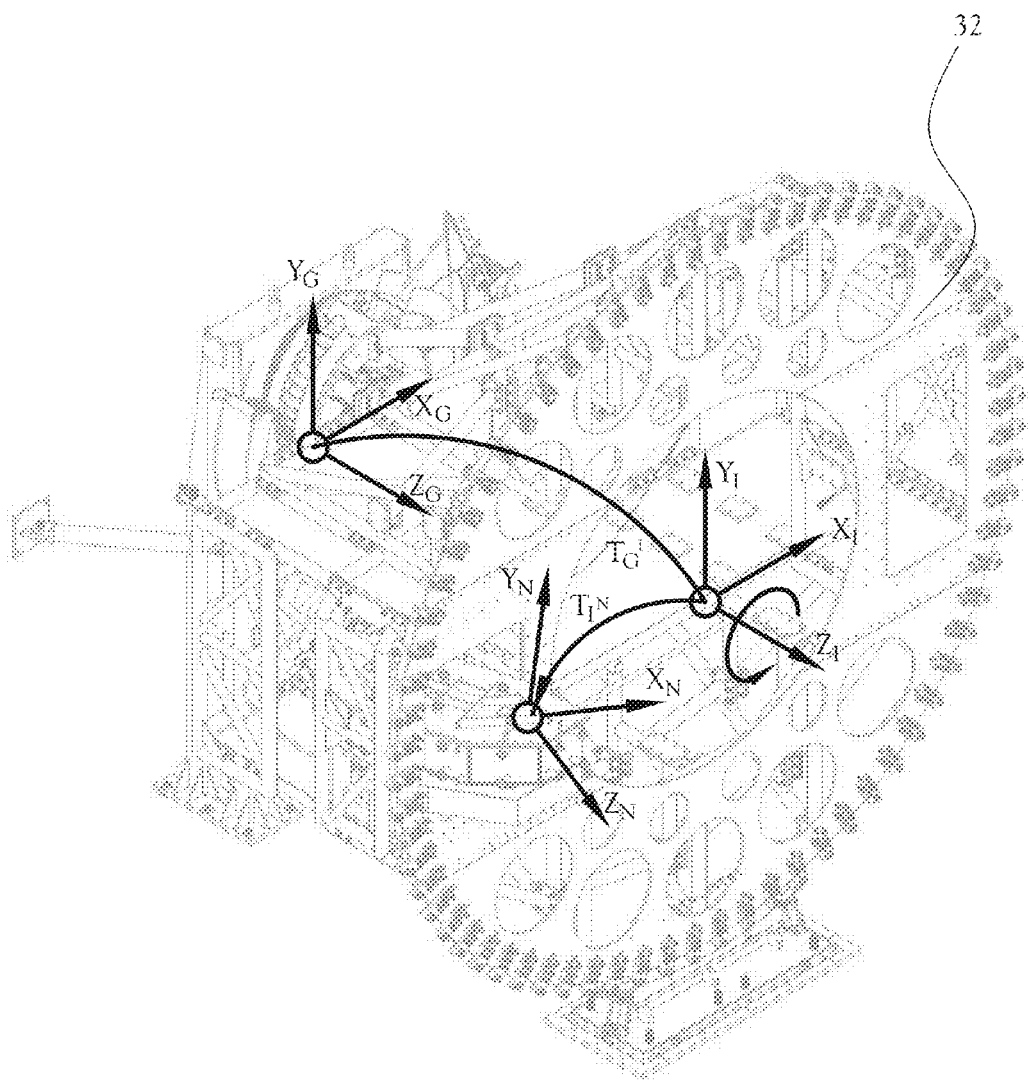
FIG. 11 illustrates the coordinate frames involved in the alignment of a gantry wheel according to an embodiment of the present general inventive concept.

FIG. 11 illustrates the coordinate frames involved in the alignment of a gantry wheel according to an embodiment of the present general inventive concept. Three frames to consider are the gantry (G), the (ideal) isocenter (I), and the nozzle (N). FIG. 11 illustrates the x,y,z coordinates of G, I, and N. As indicated in FIG. 11, raising the N frame may force $X_N$ through the isocenter, but the orientation may be wrong. Thus, a combination of cam-follower adjustments and a correction of the gantry rotation angle may be optimal to compensate for flexing. No correction of the rotation angle may require larger cam-follower adjustments. Due to flexing, most nozzle-trajectories will not pass through an ideal isocenter. As the gantry rotates, flexing introduces error in the position and orientation of the nozzle. Perfect compensation to correct for both the position and orientation error requires six degrees-of-freedom (DoF). A best-fit correction can be made by changing the three DoF that are available: one from the rotation angle of the gantry, and two from the cam-followers. (Changes to the cam-followers are not completely independent since they also cause a slight rotation around the back-bearing.) Changes to the cam-followers may make small changes to the orientation of the front of the gantry wheel 32. This change in orientation may raise/lower the gantry wheel 32, or move it right/left by very small amounts.

At any specific rotation angle, an angle correction and adjustment to the cam-followers that best compensates for the position and orientation error of the nozzle can be found. By correcting the rotation angle, the best-fit solution can be achieved with smaller cam-follower adjustments. Smaller cam-follower adjustments will allow more uniform support of the gantry wheel 32, reducing the risk of noise, vibration, wear, and discontinuities. Corrections to the rotation angle may be stored in a look-up table used by the gantry's motion control system. Changes in the orientation of the front of the gantry wheel 32 may be made by adjusting the cam-followers.

Figure 12B:
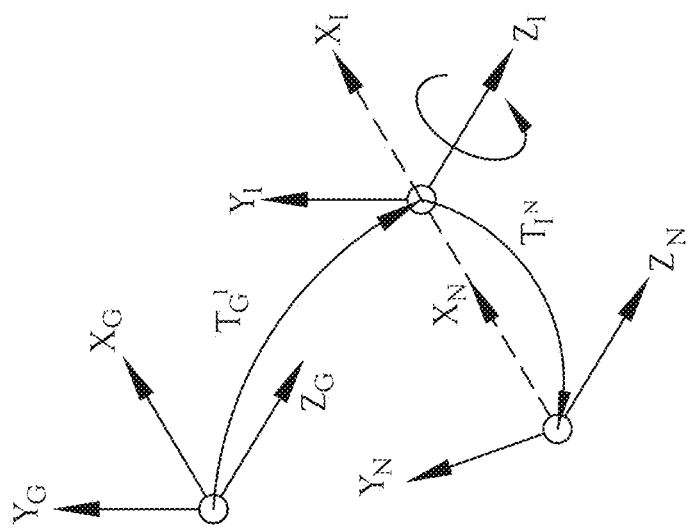
FIGS. 12A and 12B illustrate gantry alignment compensation with rotation and without rotation according to an embodiment of the present general inventive concept.
Figure 12A:
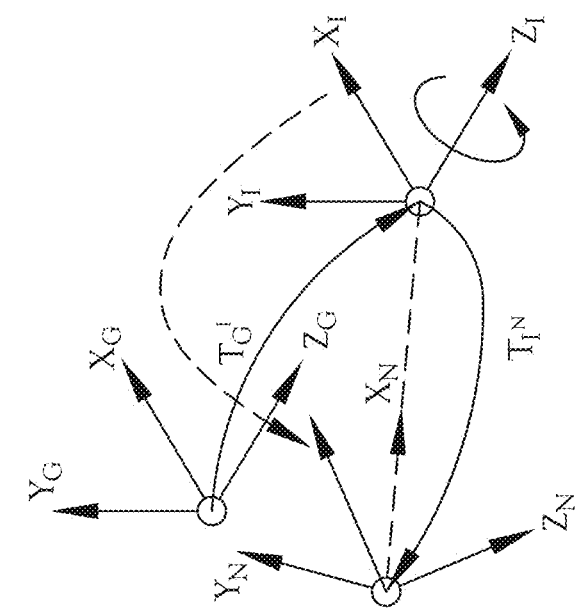

FIGS. 12A and 12B illustrate gantry alignment compensation with rotation and without rotation according to an embodiment of the present general inventive concept. As indicated by FIG. 12A, without rotation a larger correction with the cam-followers will be needed, and the orientation of the nozzle trajectory may not be correct. As indicated by FIG. 12B, with rotation a smaller correction with the cam-followers is possible, and the orientation of the nozzle trajectory is improved.

Figure 13:
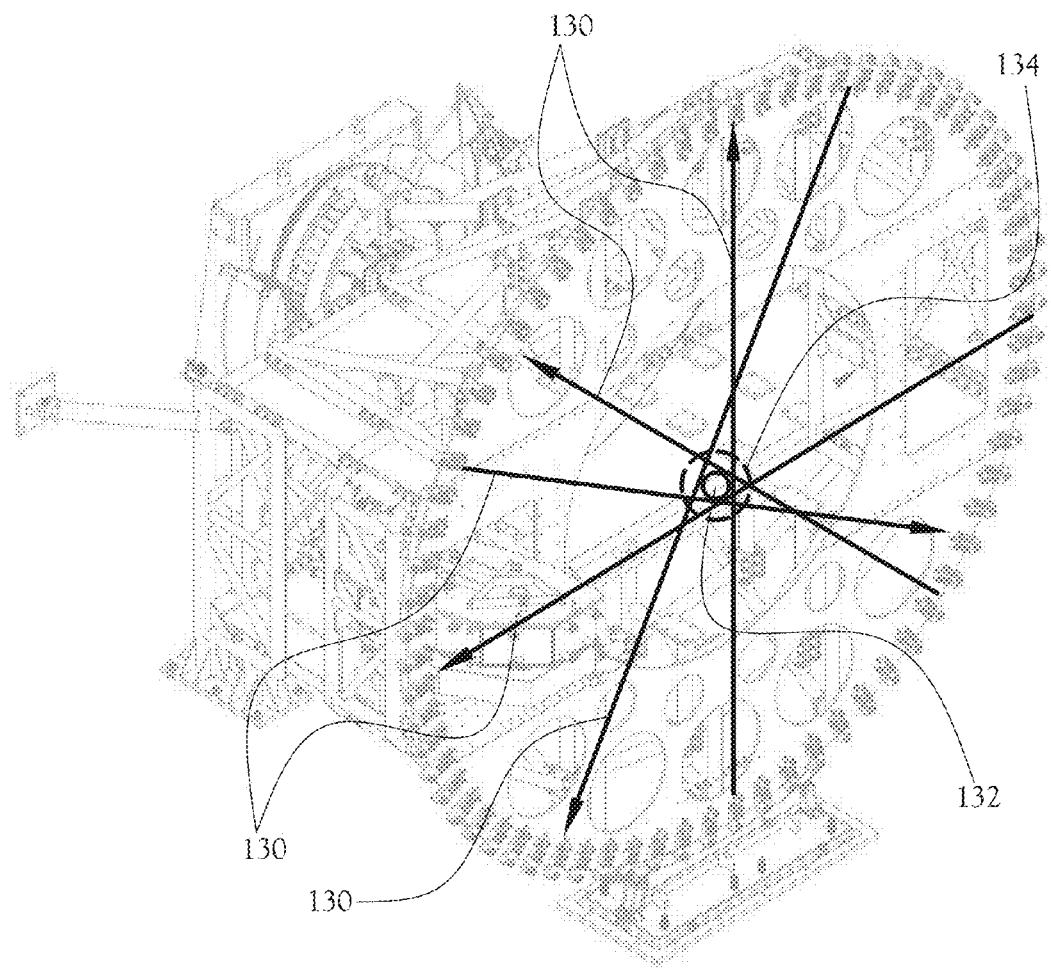
FIG. 13 illustrates nozzle trajectories and a sphere-of-confusion for a gantry system according to an embodiment of the present general inventive concept.

FIG. 13 illustrates nozzle trajectories and a sphere-of-confusion for a gantry system according to an embodiment of the present general inventive concept. As illustrated in FIG. 13, nozzle trajectories 130 to be considered in gantry modeling do not intersect perfectly, nor pass directly through the axis-of-rotation. Therefore, in gantry modeling, a precise definition for the isocenter I(x,y,z) 132 may be desired. This defined isocenter 132 should be repeatable and unique, and the possibility of whether hysteresis is a consideration may be evaluated. The Sphere-of-Confusion (SoC) 134 centered at I(x,y,z) 132 is an accepted measure of performance for a gantry system. In more detail, the process of characterizing the gantry may involve estimating the location of the isocenter 132, and determining the radius of the Sphere-of-Confusion 134. In an ideal gantry system, all nozzle-trajectories would pass through a single point, called the isocenter. Practically, however, this will likely not be the case, due to flexing. Therefore, the isocenter may be defined in a different manner. Given any point in space, the shortest distance between a point and any nozzle-trajectory is the length of a normal vector connecting the trajectory to the point. The isocenter 132 is the point that minimizes the sum of the lengths-squared of all normal vectors.

As previously described, an accepted measure of performance for a gantry is the SoC. Based on the above definition of the isocenter, the SoC is the smallest sphere centered at the isocenter that contains all the previously described normal vectors. The radius of the SoC is the length of the longest normal vector. This definition for the isocenter does not absolutely guarantee that it is a unique point. For example, two parallel nozzle-trajectories will have an infinite number of solutions for the isocenter. With many trajectories, multiple solutions for the isocenter are unlikely (but possible) since the system of equations will be over-determined. Spatial Analyzer (SA) is a software application which may be purchased with an API laser ranging system. SA provides an ad-hoc method to estimate the isocenter, but is not the true isocenter.

Figure 14:
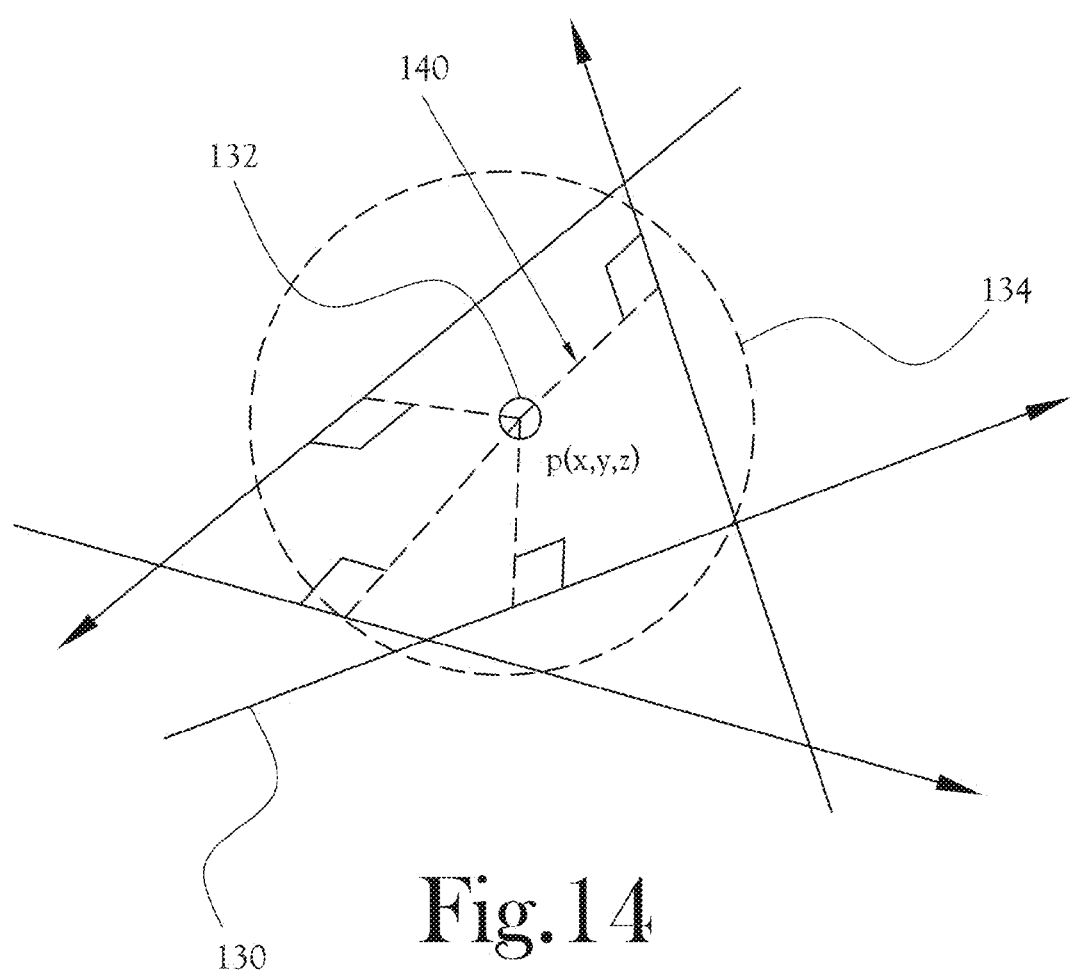
FIG. 14 illustrates a determination of the isocenter as well as the SoC resulting from three different nozzle trajectories according to an embodiment of the present general inventive concept.

FIG. 14 illustrates a determination of the isocenter I(x,y,z) as well as the SoC resulting from three different nozzle trajectories according to an embodiment of the present general inventive concept. FIG. 14 illustrates the nozzle trajectories 130, the isocenter 132, the SoC 134, and the normals with length $\epsilon_i$. As previously described, the isocenter is the point p(x,y,z) which minimizes the sum of the length-squared of all normal vectors from p to the nozzle-trajectories, as indicated by the following equation (Equation (A)):

$$I(x, y, z) = \min_{p(x,y,z)} \sum_i \|\epsilon_i\|^2 \qquad \text{Equation (A)}$$

The SoC is the smallest sphere centered at I(x,y,z) with radius $R_I$ that contains all normal to the nozzle-trajectories, as indicated by the following equation (Equation (B)):

$$R_I = \max_i \|\epsilon_i\| \qquad \text{Equation (B)}$$

An ad-hoc method for finding the SoC according to an embodiment of the present general inventive concept will now be described. It is understood that this is simply one method for estimating the isocenter, and other methods and/or software applications may be utilized instead. As previously stated, Spatial Analyzer (SA) may be used to provide an ad-hoc method to estimate the isocenter. The method according to this example embodiment of the present general inventive concept includes generating a collection of vectors from two reflectors attached to the nozzle at various rotation angles. For each pair of vectors in the collection, SA may find the point closest to each vector and save those points in a new collection of points. For the collection of points, SA may then find the center-of-mass of the points, which is an estimate of the isocenter. As will be recognized by one skilled in the art, a repeatable method may be desired to evaluate gantry flexing and evaluate hysteresis, and to make corrections to compensate for flexing.

Figure 15:
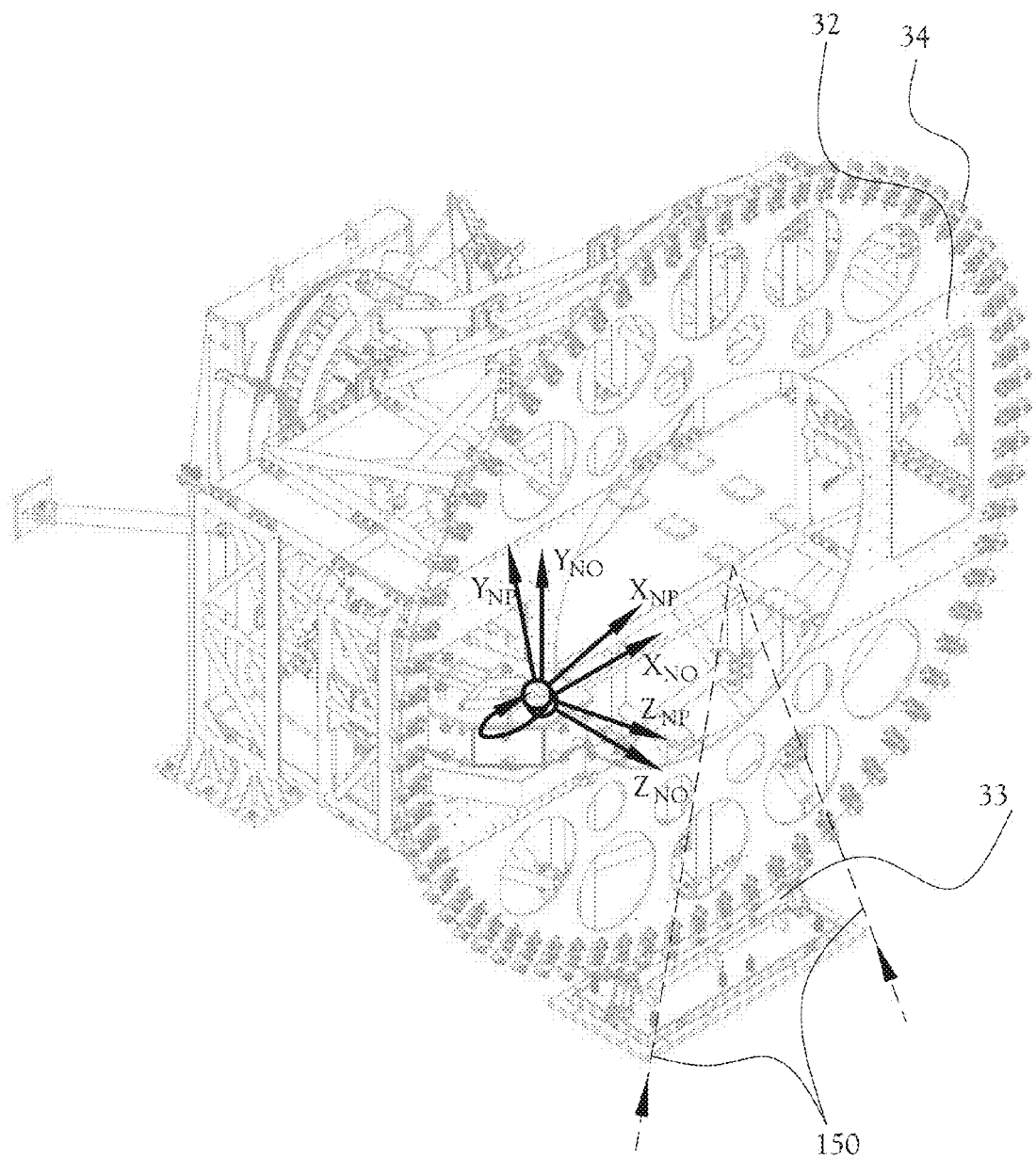
FIG. 15 illustrates a gantry flexing model and alignment process according to an embodiment of the present general inventive concept.

FIG. 15 illustrates a gantry flexing model and alignment process according to an embodiment of the present general inventive concept. In this example embodiment, it is assumed that all the cam-followers 34 are initially adjusted to the mid-point of travel, and that displacements applied with hydraulic actuators 150 can be measured. The method of this example embodiment includes, for different gantry rotation angles, applying small perturbations with each actuator (one at a time), and a small change in gantry rotation. Sensitivity functions are numerical models that describe how the nozzle changes position and orientation. These functions are relatively constant for small changes in displacement and rotation angle, and include flexing not modeled by CAD tools.

In more detail, the proposed automated gantry alignment process according to an example embodiment of the present general inventive concept may be broken down into the following phases: Characterization, Modeling, Computation, and Implementation. Characterization in this example embodiment identifies the position and orientation errors, as indicated by Np and No in FIG. 15, of the nozzle-trajectory as the gantry rotates, and estimates the gantry's center of rotation. The nozzle trajectory can be determined by measuring two points on the nozzle with the laser ranging system. Initially, as previously discussed, the gantry is characterized with all cam-followers 34 set to a neutral position (the mid-point of the adjustment range).

Modeling in this example embodiment refers to predicting how the gantry will respond to small perturbations applied with each hydraulic actuator 150, and making a small change in rotation angle. The perturbations applied with the actuators 150 change the orientation of the front of the gantry 32 (by very small amounts). The small changes in the nozzle-trajectory relative to the perturbations provide sensitivity functions, at various rotation angles around the gantry 32. These sensitivity functions form a linearized model of the gantry, and remain relatively constant at a fixed gantry angle, but will change as the gantry rotates. Since positive hydraulic actuator displacements are sufficient to estimate the sensitivities, the cam-followers do not need to be changed. This enables this phase to be fully automated, without technician interaction.

During the Computation phase of this example embodiment of the present general inventive concept the sensitivity functions may be used to predict the best rotation correction and change in orientation of the front of the gantry 32, to compensate for as much flexing as possible, at various rotation angles around the gantry 32. According to various example embodiments, the angle correction can be stored in a look-up table for later use. The orientation corrections slightly shift the center-of-rotation at the front of the gantry. As the gantry 32 rotates, these shifted centers-of-rotation trace a path. Based on this path, the gantry alignment can be "Smooth" or "Optimized." Regarding the Smooth gantry alignment, by picking one point closes to all points on the path, a new center-of-rotation can be defined that provides enhanced compensation for flexing. If the cam-followers 34 are adjusted to shift the center-of-rotation to this point, they will track a circular path as the gantry 32 rotates. In this case, the gantry 32 will be uniformly supported by the cradle 33 at all rotations angles. This will provide smooth operation, since there will be no discontinuities, and vibration will be minimized. As an alternative, in an 'Optimized' gantry alignment, the closest path that also limits the maximum rate-of-change of the center-of-rotation may be selected. In this case, which is referred to herein as an 'optimized' case (for convenience of description, and not by way of limitation), better compensation of the nozzle 30 may come at the expense of how uniformly the gantry 32 is supported by the cradle 33. Since the center-of-rotation changes as the gantry rotates, it will not be supported as uniformly. But this is controlled by limiting how much the center-of-rotation changes as a function of rotation angle.

During the Implementation phase of this example embodiment the cam-followers 34 may be adjusted. The system guides the technician to effectively make the cam-follower 34 adjustments. The basic operations include (i) rotating the gantry 32 to an angle with the rotation correction applied, (ii) raising the gantry 32 off the cam-followers 34 with the hydraulic actuators 150, (iii) moving, by the technician, the cam-followers 34 to obtain maximum clearance, (iv) correctly repositioning the gantry 32 using the hydraulics system, (v) adjusting, by the technician, the cam-followers 34 to support the gantry 32, and (vi) retracting the hydraulic actuators 150 to transfer the load back to the cam-followers 34. These operations may be repeated until all the cam-followers 34 are adjusted, at which point the Characterization (phase) may be re-evaluated.

Figure 16:
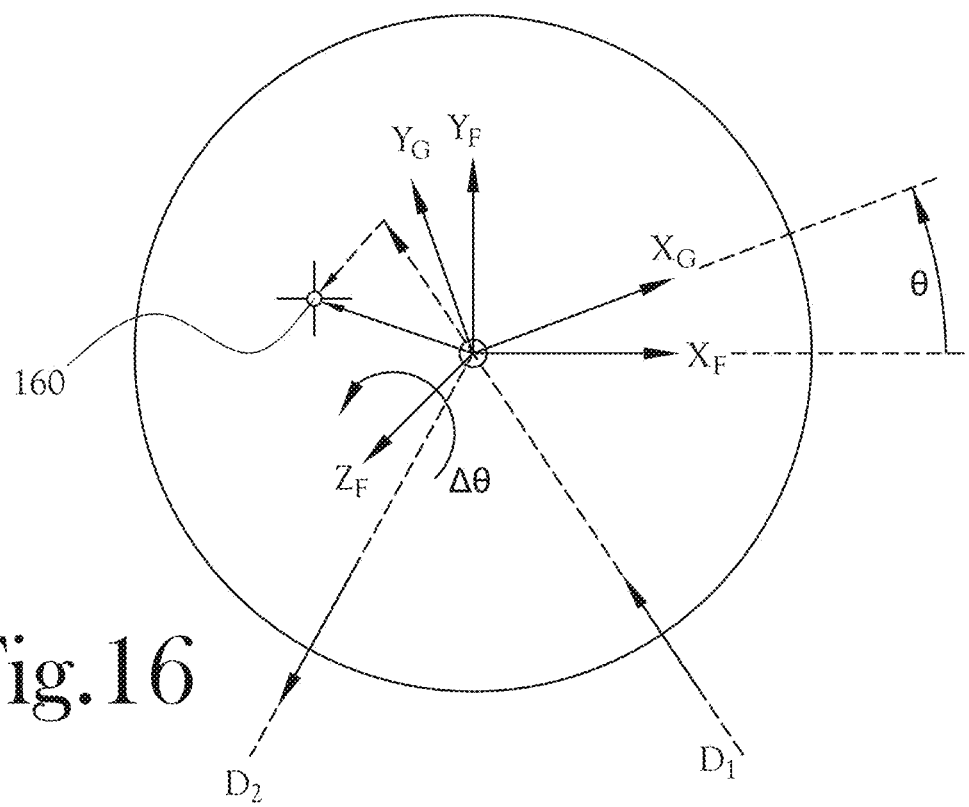
FIG. 16 illustrates a local correction for flexing according to an embodiment of the present general inventive concept.

FIG. 16 illustrates a local correction for flexing according to an embodiment of the present general inventive concept. A solution according to this example embodiment involves using the sensitivity functions to calculate, for different gantry rotation angles ($\theta$), the actuator displacements ($D_1$, $D_2$) and rotation angle correction ($\Delta\theta$) that minimize the error between the desired and resulting nozzle-trajectories (position and orientation). The Least-Squares solution is used, and a perfect correction may not be possible with only 3-DOF. The solution of this example embodiment assumes flexing does not change much for small applied corrections (linear approximation). The displacements move the center-of-rotation 160 at the front of the gantry. A rotation correction leads to smaller displacements.

Figure 17:
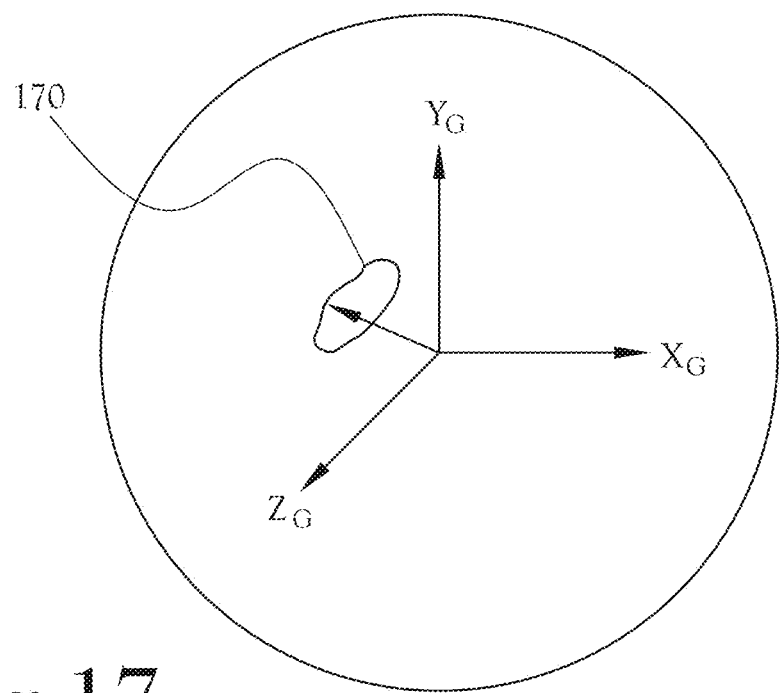
FIG. 17 illustrates a center-of-rotation path that is followed as the gantry rotates according to an embodiment of the present general inventive concept.

FIG. 17 illustrates a center-of-rotation path that is followed as the gantry rotates according to an embodiment of the present general inventive concept. Observations of the path 170 followed by the center-of-rotation as the gantry 32 rotates include that at any rotation angle $\theta$, flexing can be compensated locally by applying a correction to the gantry angle, and shifting the center-of-rotation. As the gantry rotates, the center-of-rotation at each gantry angle ($\theta$) forms a closed path.

Figure 18:
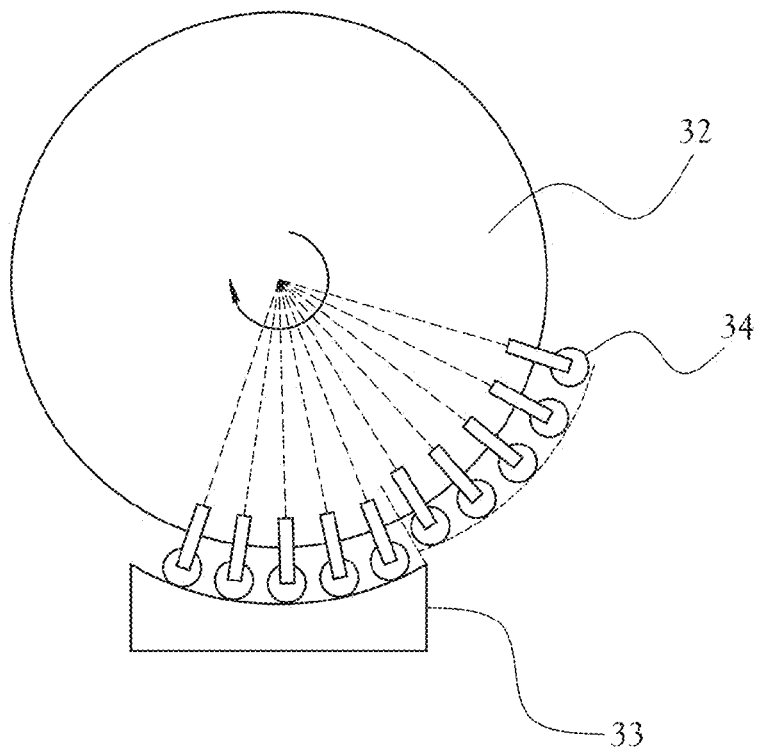
FIG. 18 illustrates discontinuities in gantry alignment which may occur of sets of cam-followers are adjusted independently.
Figure 19:
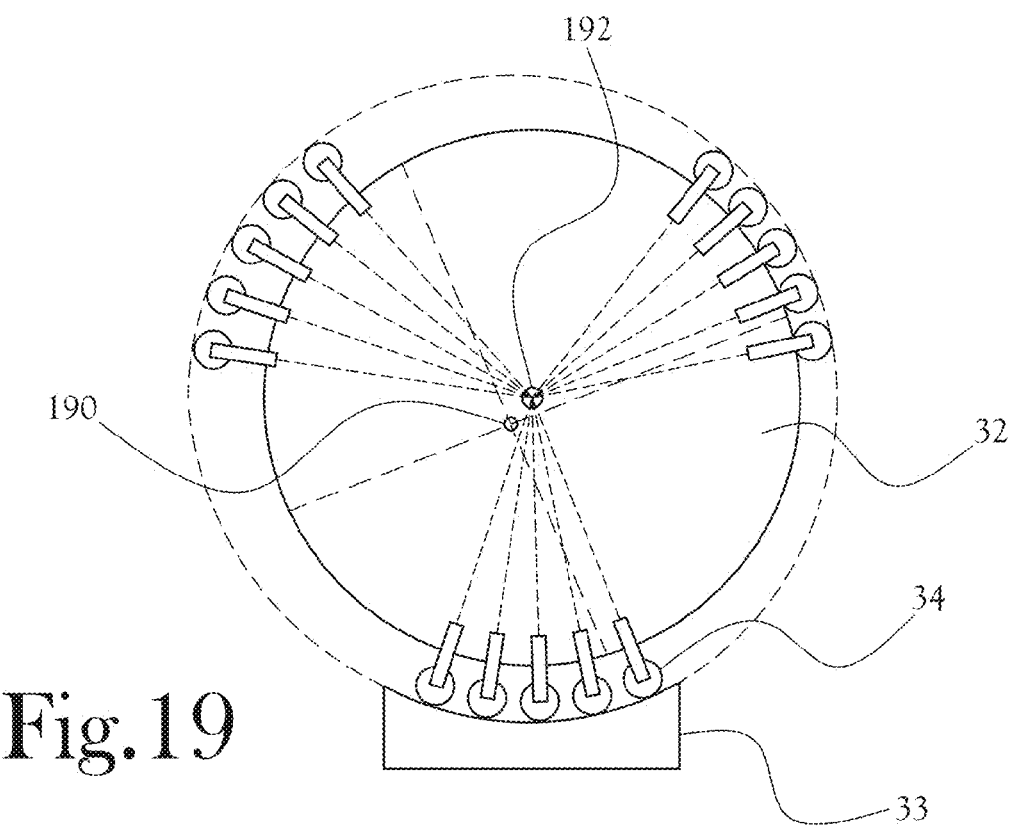
FIG. 19 illustrates and describes a gantry system with no discontinuities in alignment according to an embodiment of the present general inventive concept.

FIG. 18 illustrates discontinuities in gantry alignment which may occur of sets of cam-followers 34 are adjusted independently. Discontinuities may occur if sets of cam-followers are adjusted independently to compensate for flexing, which may cause wear, vibration, noise, and indeterminate position/orientation during the transition around the discontinuity. The example illustrated in FIG. 18 shows the front of the gantry tilted to compensate for flexing, and assumes flexing does not change much between adjacent sets of cam-followers. The same problem occurs if the gantry is raised or lowered, and not tilted.) FIG. 19 illustrates and describes a gantry system with no discontinuities in alignment according to an embodiment of the present general inventive concept. In this example, there may be no occurrence of discontinuities if the cam-followers 34 are adjusted to maintain a fixed center-of-rotation 190, as opposed to the center 192 of the gantry 32, as the gantry 32 rotates. The cam-followers 34 substantially always maintain uniform contact with the cradle 33, and may not equally share the weight.

FIG. 20 illustrates a smooth gantry alignment of an embodiment of the present general inventive concept. FIG. 20 illustrates the center-of-gantry 192 as being displaced from the center-of-rotation 160, and shows the path of center-of-rotation 170 that best compensates flexing at each gantry angle. This solution includes adjusting the cam-followers 34 to shift the center-of-rotation 190 to the location that provides maximum overall correction to the nozzle trajectory (position and orientation) as the gantry 32 rotates. This method provides no discontinuities, weights the path to give a better solution at more important rotation angles, and is smooth since the method creates no discontinuities and the cam-followers 34 maintain uniform contact with the cradle 33.

The best gantry alignment (correction for flexing) may occur if the center-of-rotation 160 follows the ideal path as the gantry rotates, but, as previously described, the cam-followers 34 may not maintain uniform contact with the cradle 33 at all angles. An optimized alignment can be found by choosing a path closest to the ideal path that is constrained to limit the rate at which the center-of-rotation 160 changes with respect to the gantry angle. There are trade-offs to consider when comparing the Smooth and Optimal gantry alignment methods. FIG. 21 illustrates graphs indicating actuator displacements ($D_1,D_2$) and gantry-angle-correction ($\Delta\theta$) to compensate for flexing, as a function of gantry rotation angle ($\theta$), according to an embodiment of the present general inventive concept. FIG. 22 illustrates the path of ideal center-of-rotation as being offset from the center-of-gantry point according to an embodiment of the present general inventive concept. The displacements shift the ideal center-of-rotation, which traces a path as the gantry rotates. The center of rotation translates by a distance determined by the following equation (Equation (C)):

$$\|D(\theta)\| = \sqrt{D_1^2(\theta) + D_2^2(\theta)} \qquad \text{Equation (C)}$$

Figure 23:
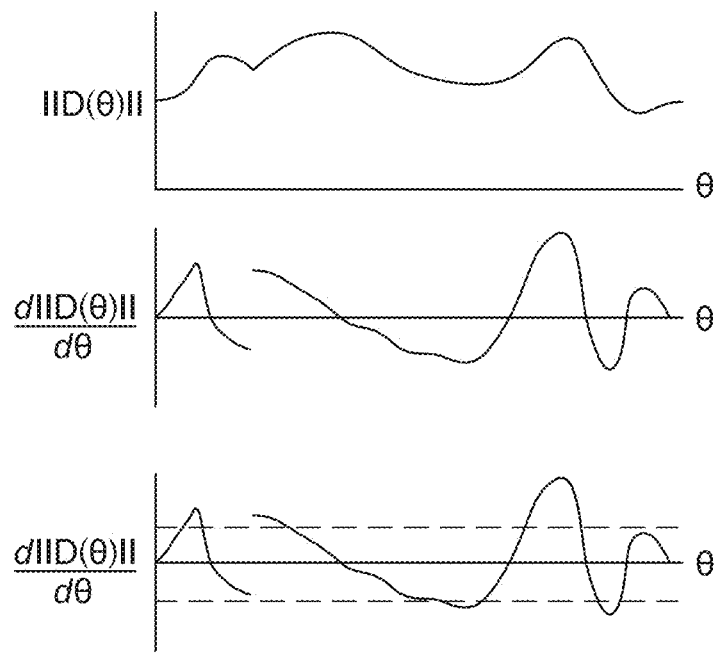
FIG. 23 illustrates graphs indicating the magnitude of the change in the center-of-rotation as the gantry rotates according to an embodiment of the present general inventive concept.
Figure 24:
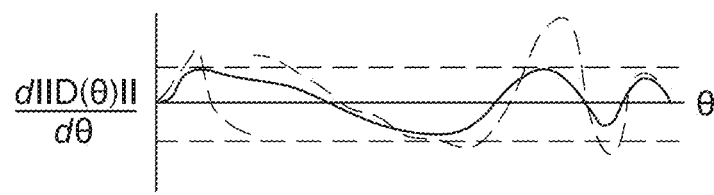
FIG. 24 illustrates a graph indicating the derivative of the magnitude of the change in the center of rotation after approximating the displacement functions with polynomials, and limiting the rate of change to an acceptable range, according to an embodiment of the present general inventive concept.
Figure 25:
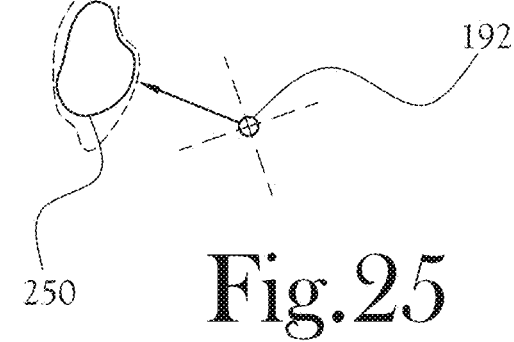
FIG. 25 illustrates the optimized path of center-of-rotation as being inside the path of ideal center-of-rotation according to an embodiment of the present general inventive concept.
Figure 26:
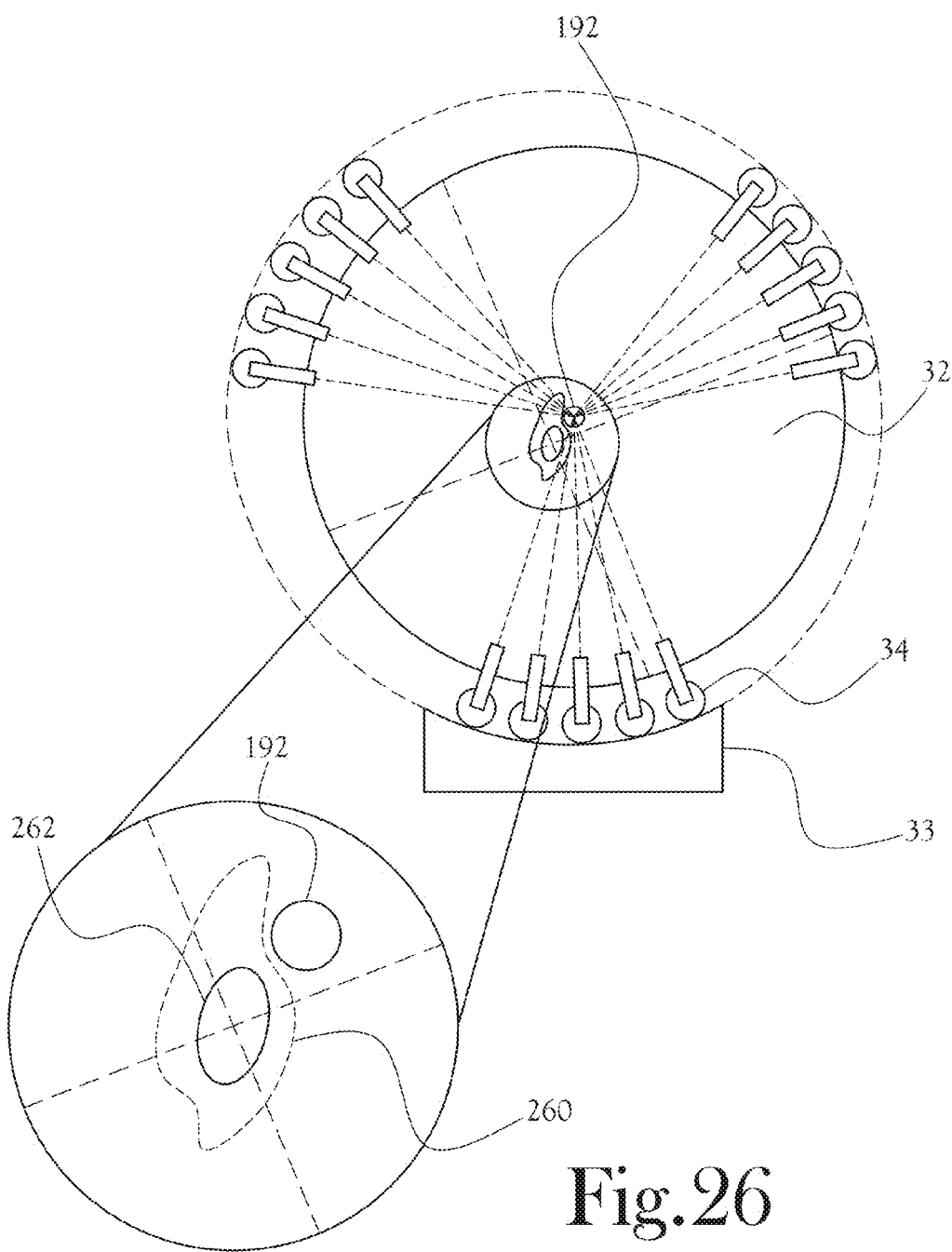
FIG. 26 further illustrates the optimal gantry alignment, and shows the adjusted positioning of some of the cam-followers that results in the optimal path that limits maximum rate-of-change of the center-of-rotation according to an example embodiment of the present general inventive concept.

FIG. 23 illustrates graphs indicating the magnitude of the change in the center-of-rotation as the gantry rotates according to an embodiment of the present general inventive concept. $\|D(\theta)\|$ is the magnitude of the change in the center-of-rotation as the gantry rotates, and the illustrated derivative shows the rate at which the center-of-rotation changes as the gantry rotates. The displacement functions ($D_1,D_2$) can be approximated with polynomials that limit the derivative of $\|D(\theta)\|$ (as bounded by the dashed lines), and ensure a continuous first derivative. The gantry will make smoother transitions as the center-of-rotation shifts to compensate for flexing. FIG. 24 illustrates a graph indicating the derivative of the magnitude of the change in the center of rotation after approximating the displacement functions with polynomials, and limiting the rate of change to an acceptable range, according to an embodiment of the present general inventive concept. FIG. 25 illustrates the optimized path 250 of center-of-rotation as being inside the path 220 of ideal center-of-rotation according to an embodiment of the present general inventive concept, and still offset from the center-of-gantry point 192. The path 250 followed by the center-of-rotation is optimized to limit how fast the center changes as the gantry 32 rotates. This provides a trade-off between the compensation for flexing and uniform support of the gantry 32. FIG. 26 further illustrates the optimal gantry alignment, and shows the adjusted positioning of some of the cam-followers that results in the optimal path that limits maximum rate-of-change of the center-of-rotation according to an example embodiment of the present general inventive concept.

As previously described, the four operations of gantry alignment according to an example embodiment of the present general inventive concept include Characterization, Modeling, Computation, and Implementation. It is understood that various example embodiments of the present general inventive concept my omit or alter one or more of the operations and/or sub-operations listed and described herein, as the present general inventive concept is not limited to this number of operations, nor the order in which they are listed or described.

The Characterization operation may include measuring the nozzle trajectory at various rotation angles ($\theta$), and estimating the isocenter and center-of-rotation. The Modeling operation may include modeling the change in nozzle-trajectory in response to small changes in hydraulic actuator displacement and rotation angle, and determining the sensitivity functions. These sensitivity functions remain relatively constant at each rotation angle, and vary as the rotation angle changes. The modeling of this example embodiment does not require any changing of the cam-followers.

The Computation operation may include determining the actuator displacements ($D_1,D_2$) and correction to rotation angle ($\Delta\theta$) that minimizes the nozzle-trajectory error (due to flexing) at each rotation angle $\theta$. The correction angles may be stored in a look-up table. The actuator displacements shift the center-of-rotation as the gantry rotates. In the Smooth alignment method, a single center-of-rotation may be chosen, and a path that limits the rate-of-change of the center-of-rotation as the gantry rotates may be chosen in the Optimized alignment method.

The Implementation operation may include guiding the technician to effectively make the cam-follower adjustments. In this example embodiment, the gantry may be rotated to an angle with rotation correction applied, and hydraulics may be employed to raise the gantry off the cam-followers. The technician moves the cam-followers to obtain maximum clearance, and the hydraulic system may be used to correctly reposition the gantry. The technician adjusts the cam-followers to support the gantry, upon completion of which the hydraulic actuators are retracted. These operations may be repeated until all the cam-followers are adjusted. In various example embodiments, the characterization operation may be repeated after the Implementation operation is completed. Also, it is noted that although a hydraulic system has been described in several of these example embodiments as the actuator system used to raise the gantry off of the cam-followers/cradle and correctly reposition the gantry, it is understood that the present general inventive concept is not limited thereto, as any number of other actuators and/or actuator systems may be used in place of, or in combination with, a hydraulic system.

Figure 27:
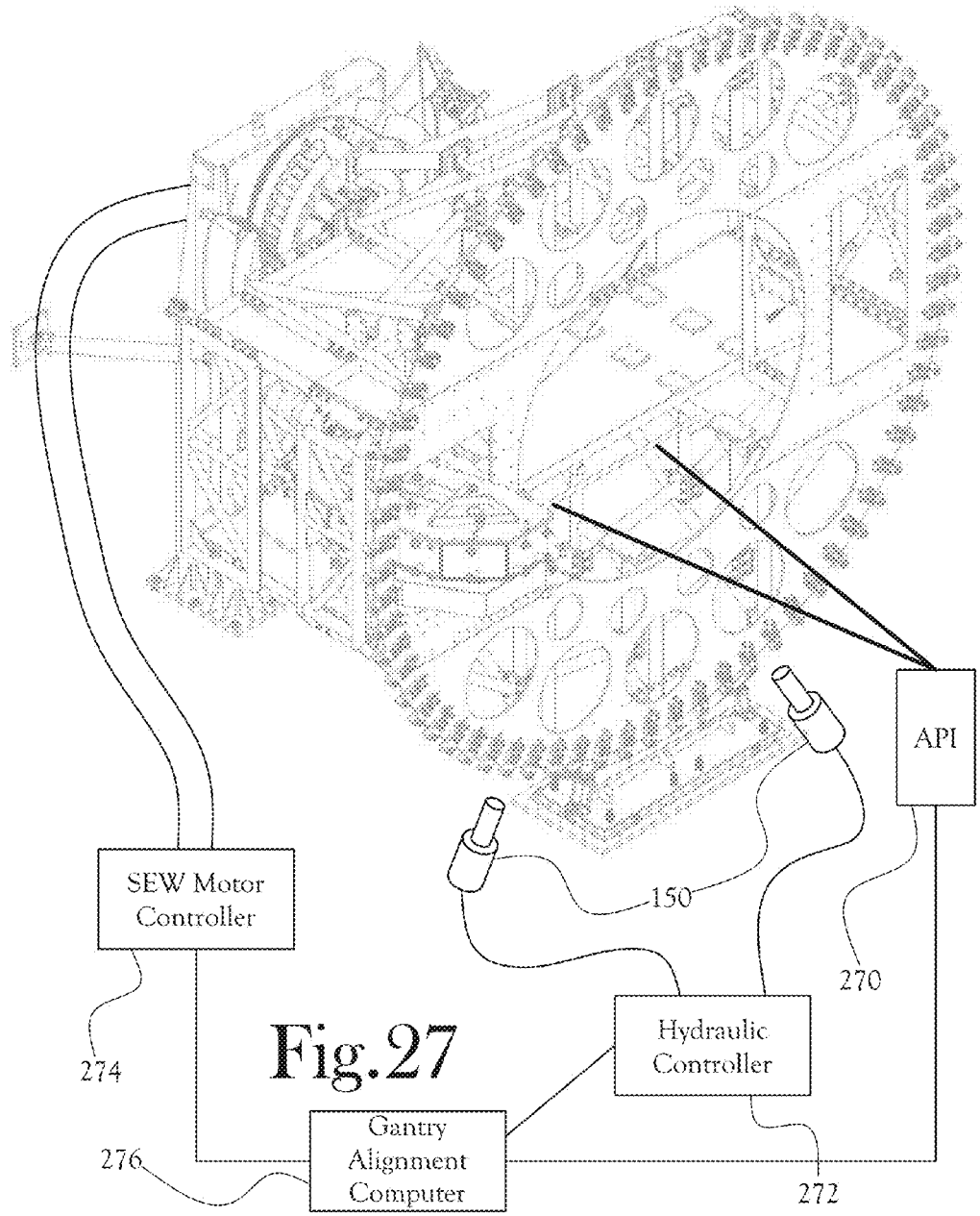
FIG. 27 illustrates various components of a gantry alignment system according to an embodiment of the present general inventive concept.

FIG. 27 illustrates various components of a gantry alignment system according to an embodiment of the present general inventive concept. The previously discussed API laser ranging system 270 may be used to measure two points on the nozzle to determine the nozzle trajectory during the estimation of the gantry's center-of-rotation. The hydraulic system, including two hydraulic actuators 150 with position encoders and a hydraulic controller 272 to control them, may be used to raise and position the gantry, and transfer the gantry back onto to the cam-followers, during the Implementation operation previously described. The SEW motor control system 274 may control the rotation of the gantry. The gantry alignment computer 276 may be in communication with the API 270, hydraulic controller 272, and SEW motor controller 274, and may coordinate the systems during the Characterization and Modeling operations of the gantry alignment, and may interface with the technician during the cam-follower adjustment. In various example embodiments of the present general inventive concept, some level of automation may be needed to assist the technician in characterizing the gantry, and then adjusting the cam-followers. The gantry is a large, heavy, complex structure that may flex in unpredictable ways. At any rotation angle, an optimal combination of angle correction and cam-follower adjustments may not be obvious. This will make any trial-and-error approach to gantry alignment difficult. An automated approach also makes the process more efficient and repeatable.

According to various example embodiments of the present general inventive concept, the gantry can be compensated for as much flexing as possible and maintain smooth operation at the same time. During the Computation operation, the actuator displacements and gantry angle corrections that best compensate the nozzle for flexing of the gantry may be determined. The angle corrections may be stored in a look-up table that will be used by the system controlling the rotation angle of the gantry. The actuator displacements shift the center-of-rotation of the gantry. Since the flexing is angle dependent, the shifted center-of-rotation also changes with gantry angle, and will trace a path as a function of rotation angle. The cam-followers can also be adjusted such that the gantry rotates around a fixed-center-of-rotation. In such a case, the cam-followers will maintain uniform contact with the cradle. By selecting the center-of-rotation that is nearest to all points in the path traced in the Computation operation, the gantry will maintain uniform contact with the cradle, and may provide improved overall compensation for errors in the nozzle trajectory due to flexing. Uniform contact between the cam-followers and cradle, at all angles of rotation, will minimize noise, vibration, and wear, and prevent discontinuities. The center-of-rotation can also be selected from a weighted set of points in the path to make a better correction for gantry angles that are more important, at the expense of the correction at other angles. This compensation method can in some cases provide the smoothest operation.

According to various other example embodiments, an alternative is to allow the center-of-rotation to change while the gantry rotates, allowing the path traced by the center-of-rotation to optimize the correction of the nozzle-trajectory. Smoother operation can be obtained by limiting the rate at which the center-of-rotation varies, as a function of the rotation angle. This allows a trade-off to be made between how well the nozzle trajectory is corrected, and how uniformly the gantry is supported by the cradle.

Figure 28:
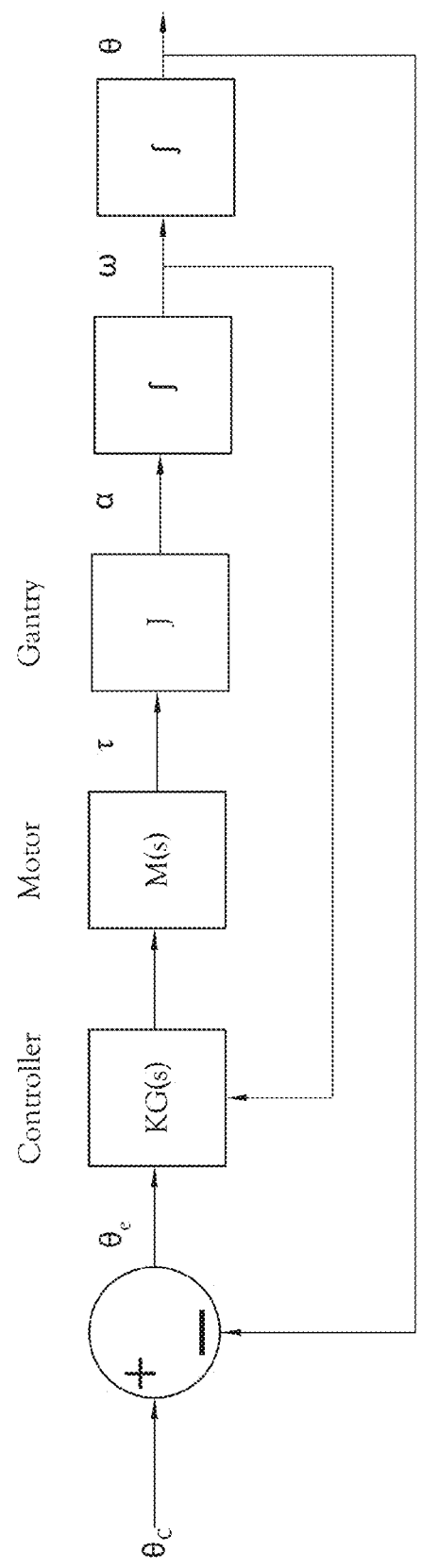
FIG. 28 illustrates a feedback control loop used to drive the gantry motors according to an example embodiment of the present general inventive concept.

FIG. 28 illustrates a feedback control loop used to drive the gantry motors according to an example embodiment of the present general inventive concept. Such a control loop may be needed to drive the motors so as to accurately rotate the gantry to the desired angle. The control loop illustrated in FIG. 28 may be more accurate in various example embodiments of the present general inventive concept than an open-loop approach. Velocity feedback may provide damping, and the controller KG(s) illustrated on page 25 may be a simple PID controller known to one skilled in the art.

Various example embodiments of the present general inventive concept discussed herein have been described as including passive cam-followers that may be adjusted by a technician when, for example, the gantry is supported by the hydraulic lifts or actuators. However, it will be understood by one skilled in the art that the present general inventive concept also contemplates utilizing actuated cam-followers, and/or the cradle itself, to move the wheel up and down, as the case may be, as the wheel rotates from angular position to angular position. Thus, various example embodiments of the present general inventive concept may include passively adjusted cam-followers, actively adjusted cam-followers, or a combination thereof.

Various example embodiments of the present general inventive concept provide a gantry alignment method and system to efficiently align a gantry system using an estimated isocenter and center-of-rotation and modeling of the changes in nozzle-trajectory in response to different rotation angles. Among the several advantages of such a system are that the Characterization and Modeling operations may be automated without changing the cam-followers, compensation for flexing may be made with corrections to the rotation angle and smaller cam-follower adjustments, cam-follower adjustments may be calculated off-line, eliminating a trial-and-error approach, the alignment may be "smooth" to prevent discontinuities, or "optimized" for better compensation of flexing at the possible expense of less-smooth operation, and guidance may be provided to a technician to make the cam-follower adjustments, making the commissioning process more efficient. Various other advantages will be recognized by those skilled in the art during the implementation of the gantry alignment system.

As described in various example embodiments of the present general inventive concept discussed above, the gantry wheel 32 rests on cam followers 34 that can be adjusted to compensate for flexing. Different methods have been proposed to adjust the cam followers 34. Various methods have been proposed to optimize nozzle trajectories, but have often assumed flexing was distributed throughout the gantry wheel 32. In various example embodiments, gantry wheel 32 rotation testing indicates a significant change in flexing may occur at the outer edge of the gantry wheel 32 near the cut-outs for the achromat and its counter-weight. Since the gantry wheel 32 is less rigid in these regions, discontinuities may occur as transitions are made between different sets of supporting cam followers 34. The discontinuities may cause noise and vibration. One solution is to add bracing to make these outer regions stiffer.

It has been suggested that the stiffness of the outer edge of the gantry wheel 32 can be modeled by springs located radially at each cam follower 34 location. A spring-based model is a linear approximation of gantry wheel 32 flexing near its edge, and can be based on empirical data. A linear model is valid for incremental changes near the operating point of a nonlinear system. To measure the spring stiffness of the gantry wheel 32, a force may be applied at each cam follower 34, and the deflection measured. The stiffness is the ratio of force over deflection. Various example embodiments of the present general inventive concept are discussed herein to describe how these stiffness parameters can be used to adjust the cam followers 34 to compensate for gantry wheel 32 flexing.

Figure 29:
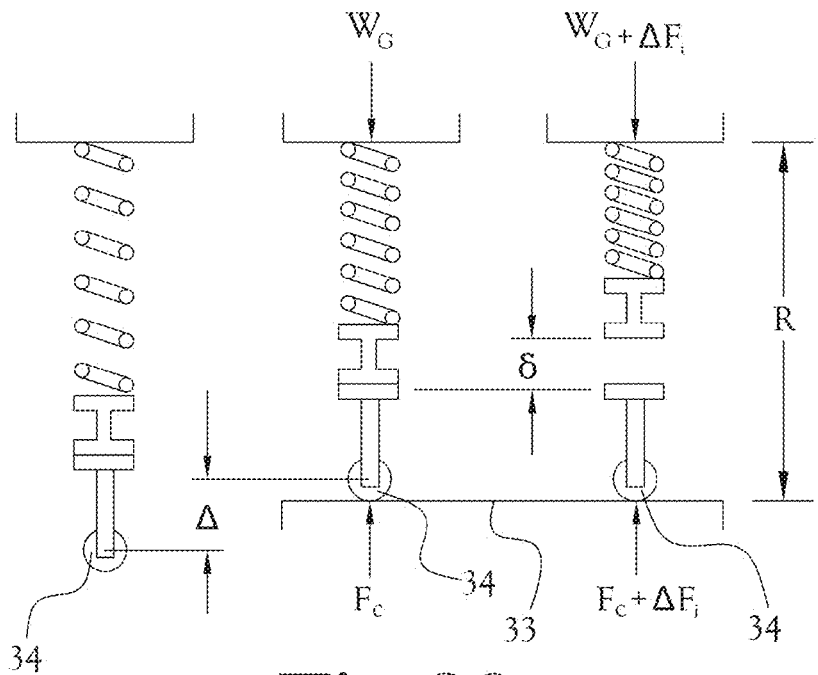
FIG. 29 illustrates a simplified linear model of gantry wheel flexing according to an example embodiment of the present general inventive concept.

FIG. 29 illustrates a simplified linear model of gantry wheel flexing according to an example embodiment of the present general inventive concept. The outer region of the gantry wheel 32 is modeled by a spring, with stiffness constant $K_i$, where i corresponds to the location of a cam follower 34 attached to the spring. The left portion of FIG. 29 illustrates this simple system floating in space, with no forces applied. In the middle portion of the illustration of FIG. 29, the weight of the gantry wheel 32 is applied, compressing the spring by $\Delta$. The force applied by the cradle 33 on the cam $F_c$ counteracts the weight of the gantry $W_G$:

$$F_c = W_G$$
$$= K_i \Delta \qquad \text{Equation (1)}$$

The term $\Delta$ represents the nominal distance the edge of the gantry wheel 32 compresses as it comes to rest in the supporting system of cam-followers 34, springs, and cradle 33.

In various example embodiments of the present general inventive concept, five or six cam followers 34 may support the gantry wheel 32, with a fixed radial dimension R. In a linear approximation, a small adjustment of one cam follower 34 does not change R since the system is constrained. In the right portion of the illustration of FIG. 29, the cam follower 34 is extended by a small amount $\delta$, further compressing the spring since it is constrained. (In the case of the gantry wheel 32, $\delta$ can also be negative.) The counteracting forces applied by the gantry wheel 32 and cradle 33 must increase by $\Delta F_i$:

$$W_G + \Delta F_i = K_i(\Delta + \delta) \qquad \text{Equation (2)}$$

Flexing is a nonlinear process. Equation (2) is the linear approximation of gantry wheel flexing at cam follower location i at the nominal operating point $\Delta$. In response to a perturbation $\delta$, the force on the cam follower and spring increases by $\Delta F_i$. A linear approximation is good if the effect of the perturbation ($\Delta F_i = K_i \delta$) does not change drastically as the operating point varies ($K_i$ remains relatively constant). In this case, the linear approximation is valid, even if $\Delta$ is not known precisely.

In a situation in which multiple cam followers 34 support the gantry wheel 32, the sum of $\Delta F_i$ for the set of supporting cam followers 34 ideally cancels. Therefore, the net force supplied by the cradle 33 is equal and opposite to the gantry wheel's weight. This assumes the gantry wheel 32 is centered relative to the back-bearing. If these forces don't cancel, they will be counteracted by whatever is constraining the gantry, such as the rear bearing.

Figure 30:
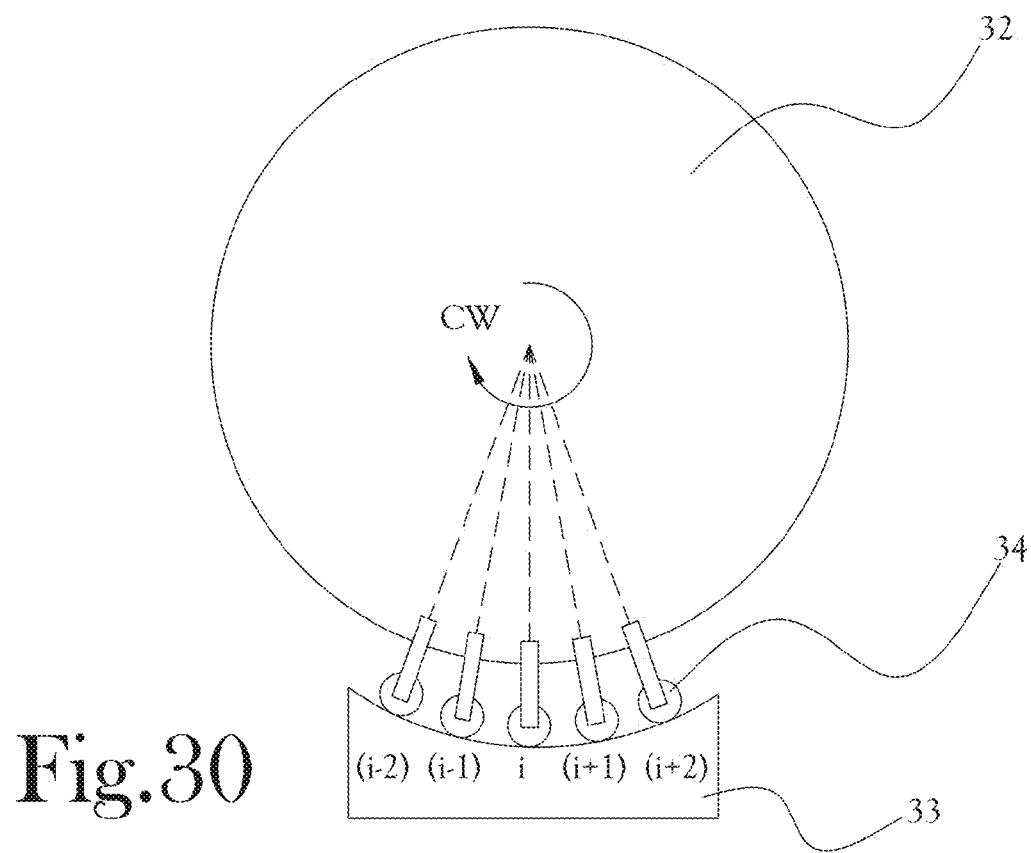
FIGS. 30-31 illustrate cam follower configurations that may be used in modeling of flexing forces according to an example embodiment of the present general inventive concept.
Figure 31:
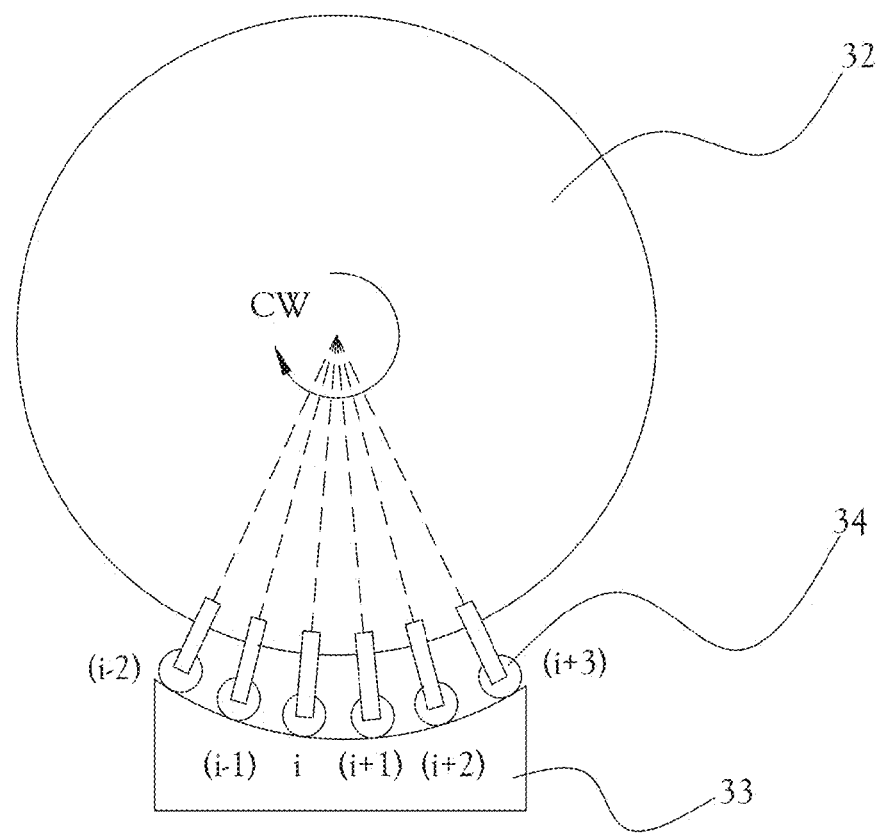

FIGS. 30-31 illustrate cam follower configurations that may be used in modeling of flexing forces according to an example embodiment of the present general inventive concept. In various example embodiments of the present general inventive concept, the gantry wheel 32 is provided with 72 cam followers 34 spaced approximately at five degree increments. In the example embodiments illustrated in FIGS. 30-31, as the gantry wheel 32 rotates, it is supported by either five or six cam followers 34, depending on the position of the gantry wheel 32. The cam followers 34 can be numbered by indices i starting at one, and increasing in the counter-clock wise direction as illustrated in FIGS. 30-31. When five cam followers 34 support the gantry wheel 32, the indices are {(i−2), (i−1), i, (i−1), (i+2)}. After the gantry wheel 32 is rotated 2.5 degrees clock-wise (CW), it will be supported by six cam followers 34. In this configuration, the six supporting cam followers 34 are {(i−2), (i−1), i, (i+1), (i+2), (i+3)}. Both configurations are associated with index i.

Figure 32:
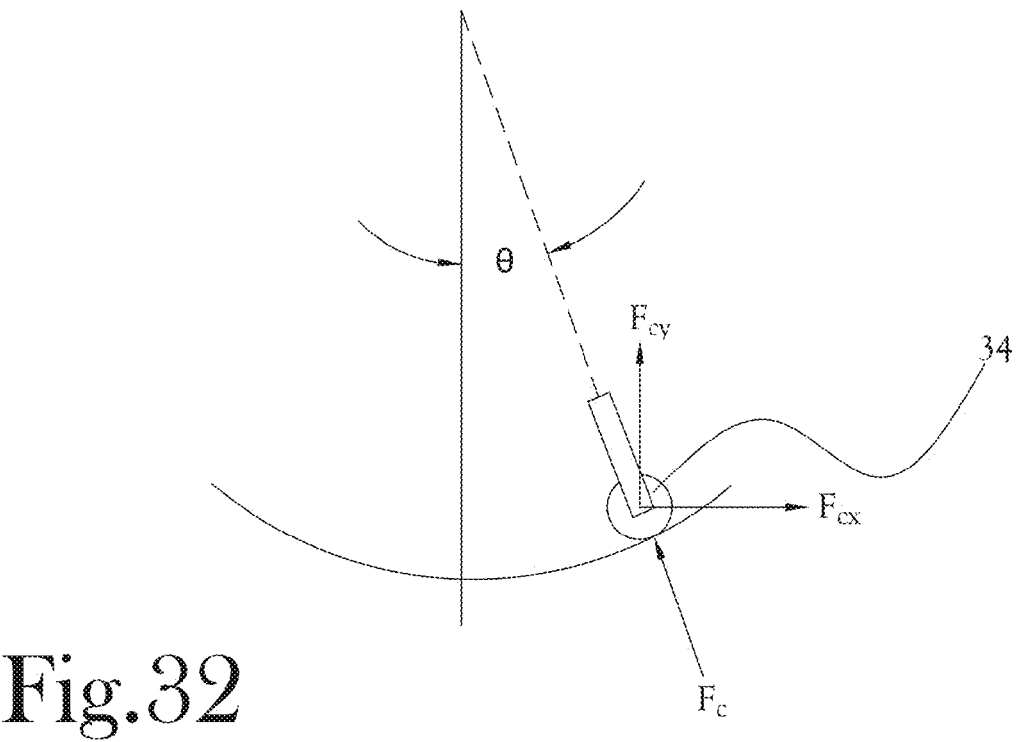
FIG. 32 illustrates a gantry wheel applying a normal force to a cam follower according to an example embodiment of the present general inventive concept.

An axis passes through the center-of-rotation of the gantry wheel 32 and each cam follower 34, and is used in the computations of the force balance equations. FIG. 32 illustrates the gantry wheel 32 applying a normal force $F_c$ to a cam follower 34 at an angle $\theta$ relative to the vertical direction. The forces in the x and y directions are:

$$F_{cx} = F_c \sin \theta$$
$$F_{cy} = F_c \cos \theta \qquad \text{Equations (3)}$$

In an arrangement in which the gantry wheel 32 is supported by five cam followers 34, the angles $\theta$ may be evaluated as occurring at (−10, −5, 0, +5, +10) degrees corresponding to the cam followers 34 {(i−2), (i−1), i, (i+1), (i+2)}. In an arrangement in which the gantry wheel 32 is supported by six cam followers 34, the angles $\theta$ may be evaluated as occurring at (−12.5, −7.5, −2.5, +2.5, +7.5, +12.5) degrees corresponding to cam followers 34 {(i−2), (i−1), i, (i+1), (i+2), (i+3)}.

Force balance equations can be written for the case when five or six cam followers 34 support the gantry wheel 32. When five cam followers 34 support the gantry wheel 32 centered around a cam follower 34 at position i, the force balance equations in the x and y directions are:

$$W_G + \Delta F_{5iy} = K_{i-2}(\Delta + \delta_{i-2})\cos(-10) +$$
$$K_{i-1}(\Delta + \delta_{i-1})\cos(-5) + K_i(\Delta + \delta_i)\cos(0) +$$
$$K_{i+1}(\Delta + \delta_{i+1})\cos(+5) + K_{i+2}(\Delta + \delta_{i+2})\cos(+10)$$

$$\Delta F_{5ix} = K_{i-2}(\Delta + \delta_{i-2})\sin(-10) +$$
$$K_{i-1}(\Delta + \delta_{i-1})\sin(-5) + K_i(\Delta + \delta_i)\sin(0) +$$
$$K_{i+1}(\Delta + \delta_{i+1})\sin(+5) + K_{i+2}(\Delta + \delta_{i+2})\sin(+10)$$

Equations (4)

When the gantry wheel 32 is rotated by 2.5 degrees CW, six cam-followers 34 support the gantry wheel 32. In this configuration, the force balance equations are:

$$W_G + \Delta F_{6iy} =$$
$$K_{i-2}(\Delta + \delta_{i-2})\cos(-12.5) + K_{i-1}(\Delta + \delta_{i-1})\cos(7.5) +$$
$$K_i(\Delta + \delta_i)\cos(-2.5) + K_{i+1}(\Delta + \delta_{i+1})\cos(+2.5) +$$
$$K_{i+2}(\Delta + \delta_{i+2})\cos(+7.5) + K_{i+3}(\Delta + \delta_{i+3})\cos(+12.5)$$

$$\Delta F_{6ix} = K_{i-2}(\Delta + \delta_{i-2})\sin(-12.5) +$$
$$K_{i-1}(\Delta + \delta_{i-1})\sin(-7.5) +$$
$$K_i(\Delta + \delta_i)\sin(-2.5) + K_{i+1}(\Delta + \delta_{i+1})\sin(+2.5) +$$
$$K_{i+2}(\Delta + \delta_{i+2})\sin(+7.5) + K_{i+3}(\Delta + \delta_{i+3})\cos(+12.5)$$

Equations (5)

In both the five and six cam configurations, the equations are referenced to cam-follower i.

A linear approximation is made at a nominal operating point of a system. Perturbations around the operating point are assumed to be small. To make the linear approximation, the following assumptions may be made: for the set of cam-followers supporting the gantry, the additional force applied by extending the cam-followers ideally sums to zero, therefore ΔF on the left of equations (4) and (5) is zero at the nominal operating point; and the parameter Δ is the displacement of the gantry wheel 32 as it gains support by the flexible outer rim through the system of springs and cam-followers 34, and represents the operating point of the system.

With these assumptions, the equations for the net force in the y direction can be simplified. To show this, one may first find two expressions for residual errors from equations (4) and (5). The residual error $e_{5iy}$ for the situation in which five cam followers 34 support the gantry wheel 32 may be defined as:

$$e_{5iy} = W_G - [K_{i-2}\cos(-10) + K_{i-1}\cos(-5) + K_i + K_{i+1}\cos(+5) + K_{i+2}\cos(+10)]\Delta \quad \text{Equation (6)}$$

In the situation in which six cam followers 34 support the gantry wheel 32, the residual error $e_{6iy}$ may be defined as:

$$e_{6iy} = W_G - [K_{i-2}\cos(-12.5) + K_{i-1}\cos(-7.5) + K_i\cos(-2.5) + K_{i+1}\cos(+2.5) + K_{i+2}\cos(+7.5) + K_{i+3}\cos(+12.5)]\Delta \quad \text{Equation (7)}$$

In terms of the residual error $e_{5iy}$, Equation (4) can then be written as:

$$\begin{bmatrix} K_{i-2}\cos(-10) & K_{i-1}\cos(-5) & K_i & K_{i+1}\cos(+5) & K_{i+2}\cos(+10) \end{bmatrix} \begin{bmatrix} \delta_{i-2} \\ \delta_{i-1} \\ \delta_i \\ \delta_{i+1} \\ \delta_{i+2} \end{bmatrix} = e_{5iy} \quad \text{Equation (8)}$$

In terms of the residual error $e_{6iy}$, Equation (5) can then be written as:

$$\begin{bmatrix} K_{i-2}\cos(-12.5) & K_{i-1}\cos(-7.5) & K_i & K_{i+1}\cos(+2.5) & K_{i+2}\cos(+7.5) & K_{i+3}\cos(+12.5) \end{bmatrix} \begin{bmatrix} \delta_{i-2} \\ \delta_{i-1} \\ \delta_i \\ \delta_{i+1} \\ \delta_{i+2} \\ \delta_{i+3} \end{bmatrix} = e_{6iy} \quad \text{Equation (9)}$$

When the gantry wheel 32 is at its nominal operating point, and a perfect solution can be found for the cam adjustments $\delta_i$, both residual errors will be zero.

From Equations (4), (6), and (8), it follows that force component $\Delta F_{5iy}$ is equivalent to the residual error $\Delta F_{5iy} = e_{5iy}$. Similarly, Equations (5), (7), and (9) show the force component $\Delta F_{6iy}$ is equivalent to the residual error $\Delta F_{5iy} = e_{5iy}$. By analogy, Equation (4) shows $\Delta F_{5ix}$ is equivalent to the residual error in the x direction in the situation in which five cam followers 34 support the gantry wheel 32, and Equation (5) shows $\Delta F_{6ix}$ is equivalent to the residual error in the x direction in the situation in which six cam followers 34 support the gantry wheel 32. When a perfect solution can be found, all residual errors are zero.

One may assume a perfect solution for the cam follower 34 adjustments cannot be found. In this case, Equations (6) and (7) provide the residual errors, based on the best estimate for Δ that is available. Equations (8) and (9) can then be combined into one matrix equation, expressed in terms of the residual errors:

$$\begin{bmatrix} K_{i-2}\cos(10) & K_{i-1}\cos(5) & K_i & K_{i+1}\cos(5) & K_{i+2}\cos(10) & 0 \\ K_{i-2}\cos(12.5) & K_{i-1}\cos(7.5) & K_i\cos(2.5) & K_{i+1}\cos(2.5) & K_{i+2}\cos(7.5) & K_{i+3}\cos(12.5) \end{bmatrix} \quad \text{Equation (10)}$$

$$\begin{bmatrix} \delta_{i-2} \\ \delta_{i-1} \\ \delta_i \\ \delta_{i+1} \\ \delta_{i+2} \\ \delta_{i+3} \end{bmatrix} = \begin{bmatrix} e_{5iy} \\ e_{6iy} \end{bmatrix}$$

The 2×6 matrix on the left of Equation (10) may be represented by $K_{1-2,i+3}$, the 6-element vector of cam follower 34 adjustments may be represented by $\underline{\delta}_{i-2,i+3}$, and the two element residual-error may be represented by vector $\underline{e}_i$. There are 72 sets of these equations for cam-followers for i=1, 2, . . . 72.

The matrices $K_{1-2,i+3}$ can be organized into one large matrix K. To show this, first note that the two element residual-error vectors can be combined into one 144-element residual error vector $\underline{E}$:

$$E = \begin{bmatrix} \underline{e}_1 \\ \underline{e}_2 \\ \vdots \\ \underline{e}_{72} \end{bmatrix} \quad \text{Equation (11)}$$

As the index i increases, the indices of the cam-follower adjustments increase. These adjustments can be lumped together into one 72-element cam-follower adjustment $\underline{\delta}$ vector:

$$\underline{\delta} = \begin{bmatrix} \delta_{71} \\ \delta_{72} \\ \delta_1 \\ \delta_2 \\ \vdots \\ \delta_{70} \end{bmatrix} \quad \text{Equation (12)}$$

The vector $\underline{\delta}$ starts with cam followers 34 located at positions 71, 72, 1, and then ends with position 70. The sub-matrices $K_{i-2,i+3}$ should line up with the cam follower 34 adjustment in $\underline{\delta}$.

The matrix K may be organized as follows:

$$K = \begin{bmatrix} [ & K_{71,4} & & ] & 0 & 0 & 0 & & & & & & 0 & 0 \\ 0 & [ & K_{72,5} & & ] & 0 & 0 & & & & & & 0 & 0 \\ 0 & 0 & [ & K_{1,6} & & ] & 0 & \cdots & & & & & 0 & 0 \\ 0 & 0 & 0 & [ & K_{2,7} & & ] & & & & & & 0 & 0 \\ & & & & & & & & & & & & 0 & 0 \\ & & & & \vdots & & & & \ddots & & & & \vdots & \\ [K_{66,71}]_6 & 0 & 0 & 0 & 0 & 0 & 0 & 0 & 0 & 0 & 0 & 0 & [ & K_{66,71} & ]_{1-5} \\ [K_{67,72} & ]_{5-6} & 0 & 0 & 0 & 0 & 0 & 0 & 0 & 0 & 0 & 0 & [ & K_{67,72} & ]_{1-4} \\ [ & K_{68,1} & ]_{4-6} & 0 & 0 & 0 & 0 & 0 & 0 & 0 & 0 & 0 & [ & K_{68,1} & ]_{1-3} \\ [ & K_{69,2} & & ]_{3-6} & 0 & 0 & 0 & 0 & 0 & 0 & 0 & 0 & 0 & [K_{69,2} & ]_{1-2} \\ [ & & K_{70,3} & & ]_{2-6} & 0 & 0 & 0 & 0 & 0 & 0 & 0 & 0 & 0 & [K_{70,3}]_1 \end{bmatrix} \quad \text{Equation (13)}$$

The dimension of the matrix K of Equation (13) is 144 rows by 72 columns. The organization of $\underline{\delta}$ requires the $K_{i-2,i+3}$ sub-matrices in the bottom five rows to be split across columns. The sub-scripts on $[K_{i-2,i+3}]_{m-n}$ imply it contains columns m through n.

A simple linear relationship exists between the residual-error vector and cam follower 34 adjustments:

$$\underline{E} = K\underline{\delta} \quad \text{Equation (14)}$$

The expression in Equation (14) contains 72 unknown cam follower 34 adjustments and 144 equations. Since this system of equations is over-determined, a perfect solution may not exist (unless the equations are trivial). Any other solution $\underline{\hat{\delta}}$ leads to an error vector $\underline{\epsilon}$:

$$\underline{\epsilon} = \underline{E} - K\underline{\hat{\delta}} \quad \text{Equation (15)}$$

The Singular-Value-Decomposition can be used to find the solution that minimizes the least-squares error $\|\underline{\epsilon}\|^2$. The SVD of K is:

$$K = U\Sigma V^T \quad \text{Equation (16)}$$

Matrices U and V are orthonormal, and represent rotations of coordinate frames. In terms of the number of rows (r) and columns (c) of K, U has a row/column dimension (r×r), $\Sigma$ has dimension (r×c), and V has dimension (c×c). Matrix $\Sigma$ contains the singular-values $\sigma_i$ of K on the diagonal. When the number of rows is greater than the number of columns, $\Sigma$ has the following structure:

$$\Sigma = \begin{bmatrix} \sigma_1 & & & \\ & \sigma_2 & & \\ & & \ddots & \\ & & & \sigma_c \\ 0 & 0 & \cdots & 0 \\ 0 & & & \\ \vdots & & \ddots & \\ 0 & & & 0 \end{bmatrix} = \begin{bmatrix} \Sigma_u \\ [0] \end{bmatrix} \quad \text{Equation (17)}$$

The (c×c) sub-matrix $\Sigma_u$ represents the non-zero partition of $\Sigma$. The singular values are arranged from largest to smallest values, and are always positive.

The least-squares solution for the cam follower 34 adjustments is given by:

$$\underline{\hat{\delta}} = [V\Sigma^\dagger U^T]\underline{E} \quad \text{Equation (18)}$$

In Equation (18) above, the term in brackets is the generalized inverse of K. $\Sigma^\dagger$ is the transpose of $\Sigma$ with inverted singular values. If any singular values are close to zero (within the machine precision), they are set to zero. The $\Sigma^\dagger$ matrix is as follows:

$$\Sigma = \begin{bmatrix} 1/\sigma_1 & & & 0 & 0 \\ & 1/\sigma_2 & & & \\ & & \ddots & & \\ & & & 1/\sigma_c & 0 & 0 \end{bmatrix} = \quad \text{Equation (19)}$$

$$[\Sigma_u^\dagger \quad [0]]$$

The matrix U can be partitioned into right and left sub-matrices:

$$U = [U_l U_r] \quad \text{Equation (20)}$$

In Equation (20), $U_l$ has dimension (r×c). The solution in Equation (18) can then be found without unnecessary multiplications by zero:

$$\underline{\hat{\delta}} = [V\Sigma_u^\dagger U_l^T]\underline{E} \quad \text{Equation (21)}$$

In various example embodiments of the present general inventive concept, the cam followers 34 can be adjusted to compensate for local flexing of the gantry wheel 32. However, since the cam followers 34 are coupled by their common attachment to the gantry wheel 32, one may wish to adjust the cam followers 34 as a system. An exemplary solution is given by Equation (21). A perfect solution was described as all sets of supporting cam followers 34 contributing no additional forces to be countered by the system constraints. Since the solution is not perfect, stress concentrations occur when the cam followers 34 compensate for flexing. Given the solution for $\underline{\hat{\delta}}$ arrived at with Equation (21), these additional forces can be determined from Equations (4) and (5).

To quantify the effect of such a solution in the y direction, terms related to the weight can be subtracted from both equations. When five cams followers 34 support the gantry wheel 32, the y component of force due to the imperfect solution is:

$$\Delta F_{5iy} = K_{i-2}(\delta_{i-2})\cos(10) + K_{i-1}(\delta_{i-1})\cos(5) + \quad \text{Equation (22)}$$
$$K_i(\delta_i) + K_{i+1}(\delta_{i+1})\cos(5) + K_{i+2}(\delta_{i+2})\cos(10)$$

When six cam followers 34 support the gantry wheel 32, the y component of additional force is:

$$\Delta F_{6iy} = K_{i-2}(\delta_{i-2})\cos(12.5) + K_{i-1}(\delta_{i-1})\cos(7.5) + \quad \text{Equation (23)}$$
$$K_i(\delta_i)\cos(2.5) + K_{i+1}(\delta_{i+1})\cos(2.5) +$$
$$K_{i+2}(\delta_{i+2})\cos(7.5) + K_{i+3}(\delta_{i+3})\cos(12.5)$$

These forces are not directly dependent on the gantry weight and nominal operating point, $\Delta$.

The x components of force depend on the weight of the gantry wheel 32, $W_G$, through the $\Delta$ term. When five cam followers 34 support the gantry wheel 32, the x component of force due to the imperfect solution is:

$$\Delta F_{5ix} = -K_{i-2}(\Delta + \delta_{i-2})\sin(10) - K_{i-1}(\Delta + \delta_{i-1})\sin(5) + \quad \text{Equation (24)}$$
$$K_{i+1}(\Delta + \delta_{i+1})\sin(+5) + K_{i+2}(\Delta + \delta_{i+2})\sin(+10)$$

In the situation in which six cam followers 34 support the gantry wheel 32, the x component of additional force is:

$$\Delta F_{6ix} = \quad \text{Equation (25)}$$
$$-K_{i-2}(\Delta + \delta_{i-2})\sin(-12.5) - K_{i-1}(\Delta + \delta_{i-1})\sin(-7.5) -$$
$$K_i(\Delta + \delta_i)\sin(-2.5) + K_{i+1}(\Delta + \delta_{i+1})\sin(+2.5) +$$
$$K_{i+2}(\Delta + \delta_{i+2})\sin(+7.5) + K_{i+3}(\Delta + \delta_{i+3})\cos(+12.5)$$

Although the expressions for $\Delta F_{5ix}$ and $\Delta F_{6ix}$ include the weight of the gantry wheel 32, some cancellation occurs due to the sign differences.

When cam followers 34 are adjusted to compensate for flexing of the constrained gantry wheel 32, counter forces that add additional stress are unavoidable. In various example embodiments of the present general inventive concept, the solution given by Equation (21) produces the least additional stress.

The operating point of the gantry wheel 32, $\Delta$, is the nominal deflection as it comes to rest in the cradle. It can be estimated based on the stiffness constants of the gantry wheel 32 and weight. A precise value is difficult to determine. However, a precise value may not be needed if the stiffness constants of the gantry wheel 32 ($K_i$) do not change drastically for small variations of $\Delta$.

In various example embodiments of the present general inventive concept, the cam followers 34 have a limited adjustment range. In certain example embodiments, the axis between the theoretical center of the gantry wheel 32 and the rear bearing may ideally be orthogonal to the surface of the bearing, when the cam followers 34 are set to a correct default extension. The adjustment range for the cam followers 34 may be based on how much mechanical error was expected in fabricating the gantry wheel 32, a best guess of the additional range needed to compensate for flexing, etc. These default cam follower 34 adjustments may be assumed to be known.

Let $\Delta_0$ be an initial guess for the nominal value of gantry deflection. The cam follower 34 deflections can be determined from Equation (21) using $\Delta_0$ as the nominal operating point. If $\Delta_0$ is close to being correct, the average deflection should be close to the cam follower 34 deflection based on the gantry design. If it isn't, a simple sensitivity analysis of $\Delta$ can be performed to estimate how it should be adjusted to derive the next estimate, $\Delta_1$. This process can be repeated until the estimates convergence to a final value $\Delta_f$. Even if $\Delta_f$ is not known to an exact value, it is likely to be close enough that a favorable set of cam follower 34 adjustments can be determined. This is the case if small changes in $\Delta$ do not significantly change the stiffness constants $K_i$.

The various example embodiments of the present general inventive concept described above suggest a method to predict cam follower adjustments to compensate for gantry wheel flexing. In various example embodiments, since the cam followers interact, there may be no perfect solution that supports the gantry wheel with complete uniformity, at all rotation angles. Stiffening the gantry wheel may lead to smaller adjustments, and smoother operation. Since some residual flexing will always occur, the proposed method provides a reasonable alternative to estimate a favorable set of cam follower adjustments.

Given the complexities and assumptions required for an idealized solution, a simplified alignment method was developed that accounts for many of the variations in mechanical dimensions and in material properties. According to various example embodiments of the present general inventive concept, this example method starts with the gantry wheel 32 in the 9 o'clock position as in FIG. 11. To be considered "aligned" from this orientation the projection of the $X_N$ axis must intersect with $Z_I$ which then must intersect with $Z_G$. At the 9 o'clock position, the deflection is solely in the Y axis (either $Y_G$ or $Y_I$). The cam followers 34 are adjusted until the $X_N$ intersection of $Z_I$ and $Z_G$ is within tolerance. The distance between $X_N$ and $Z_I$ becomes the primary scalar value for adjustment. Hence, when the gantry is rotated a few degrees, the interfacing cam followers 34 are adjusted until the radius from $X_N$ to $Z_I$ matches the original distance between those points at 9 o'clock. This process is repeated around the full 360 degrees of rotation.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A gantry wheel adjustment system to adjust a gantry wheel of a proton treatment system, the proton treatment system comprising a proton beam nozzle to direct a proton beam to an isocenter of the gantry wheel, a plurality of adjustable bearings incrementally spaced apart along an outer diametrical surface of the gantry wheel, and a bearing surface to receive a portion of the adjustable bearings such that the gantry wheel is supported on the bearing surface by the portion of adjustable bearings received thereon, the gantry wheel adjustment system comprising:

an estimation unit to estimate a bearing adjustment value for each of the adjustable bearings based on a stiffness parameter of each adjustable bearing, the stiffness parameter being a function of a force applied at each adjustable bearing and a deflection of the gantry wheel associated with the force applied at each adjustable bearing, the bearing adjustment value corresponding to a nominal position value for each adjustable bearing to compensate for gantry wheel flexing when the gantry wheel is rotated from a first angular position to a second angular position, the adjustable bearings being configured to support the gantry wheel on the bearing surface and maintain the proton beam at the isocenter of the gantry wheel during gantry wheel rotation.

2. A gantry apparatus for a proton treatment system, comprising:
 a proton beam nozzle to emit a proton beam to a targeted region of a patient;
 a gantry wheel to support the proton beam nozzle to direct the proton beam to an isocenter of the gantry wheel corresponding to a center of the targeted region;
 a plurality of adjustable bearings incrementally spaced apart along an outer diametrical surface of the gantry wheel;
 a bearing surface to support a portion of the adjustable bearings such that when the gantry wheel is rotated from a first angular position to a second angular position, at least a portion of the bearings contact the bearing surface to raise or lower the gantry wheel to realign the proton beam to the center of the targeted region;
 a deflection measuring unit to measure a deflection value of the gantry wheel at each adjustable bearing according to a force applied to each of the adjustable bearings; and
 a nominal positioning unit to determine a nominal value of gantry wheel compression at each adjustable bearing according to the deflection value.

3. The gantry apparatus of claim 2, further comprising a position determination unit to determine initial positions for each of the adjustable bearings, the initial positions being achieved by extending the respective adjustable bearings to a corresponding length.

4. The gantry apparatus of claim 3, further comprising a linear approximation unit to approximate gantry wheel flexing at each adjustable bearing position.

5. The gantry apparatus of claim 4, wherein the linear approximation unit approximates the gantry wheel flexing for a plurality of the adjustable bearings that will be simultaneously contacting the bearing surface.

6. The gantry apparatus of claim 5, wherein the linear approximation unit approximates the gantry wheel flexing according to the sum of forces acting on the adjustable bearings contacting the bearing surface by the bearing surface being equal to the weight of the gantry wheel.

7. The gantry apparatus of claim 5, wherein the linear approximation unit approximates the gantry wheel flexing for five or six adjustable bearings simultaneously contacting the bearing surface at five degree incremental spacing.

8. The gantry apparatus of claim 5, wherein the linear approximation unit determines force balance equations in x and y directions for each of adjustable bearings contacting the bearing surface.

9. The gantry apparatus of claim 8, wherein the linear approximation unit determines residual errors according to force balance equations determined for configurations including both five and six adjustable bearings contacting the bearing surface.

10. A method of aligning a gantry apparatus for a proton treatment system, the method comprising:
 measuring a weight of a gantry wheel on a bearing surface, the gantry wheel being configured to rotate and being supported on the bearing surface by a plurality of adjustable bearings;
 measuring a corresponding deflection of the gantry wheel according to a force respectively applied to each of the adjustable bearings; and
 determining a nominal operation point of the gantry wheel according to the measured weight and deflections.

11. The method of claim 10, further comprising determining initial positions for each of the adjustable bearings, the initial positions being achieved by extending the respective adjustable bearings to a corresponding length.

12. The method of claim 11, further comprising approximating, by a linear approximation unit, gantry wheel flexing at each adjustable bearing position at the nominal operation point.

13. The method of claim 12, wherein the linear approximation unit approximates the gantry wheel flexing for a plurality of the adjustable bearings that will be simultaneously contacting the bearing surface.

14. The method of claim 13, wherein the linear approximation unit approximates the gantry wheel flexing according to the sum of forces acting on the adjustable bearings contacting the bearing surface by the bearing surface being equal to the weight of the gantry wheel.

15. The method of claim 13, wherein the linear approximation unit approximates the gantry wheel flexing for five or six adjustable bearings simultaneously contacting the bearing surface at five degree incremental spacing.

16. The method of claim 13, wherein the linear approximation unit determines force balance equations in x and y directions for each of adjustable bearings contacting the bearing surface.

17. The method of claim 16, wherein the linear approximation unit determines residual errors according to force balance equations determined for configurations including both five and six adjustable bearings contacting the bearing surface.

18. A method of aligning a gantry apparatus for a proton treatment system, the method comprising:
 establishing an isocenter of a gantry wheel;
 rotating the gantry wheel such that a proton beam nozzle provided to the gantry wheel is at a predetermined position;
 adjusting a plurality of adjustable bearings provided to the gantry wheel and that are interfacing with a support surface until a projection from the proton beam nozzle is within a predetermined tolerance from both an axis of the gantry wheel and the isocenter;
 determining a primary adjustment value as a distance between the projection from the proton beam and the isocenter after adjustment at the predetermined position;
 rotating the gantry wheel a predetermined number of degrees and adjusting the interfacing adjustable bearings until the primary adjustment value is reached between the projection from the proton beam nozzle and the isocenter at each subsequent gantry wheel position; and
 repeating the rotation and adjustment until a full 360 degrees of rotation has been reached.

19. The method of claim 18, wherein the predetermined position of the proton beam nozzle is a 9 o'clock position relative to the gantry wheel.

20. A gantry wheel adjustment system to adjust a gantry wheel of a proton treatment system, the proton treatment system comprising a proton beam nozzle to direct a proton beam to an isocenter of the gantry wheel, a plurality of adjustable bearings incrementally spaced apart along an outer diametrical surface of the gantry wheel, and a bearing surface to receive a portion of the adjustable bearings such that the gantry wheel is supported on the bearing surface by the portion of adjustable bearings received thereon, the gantry wheel adjustment system comprising:
- a rotation controller to rotate the gantry wheel such that the proton beam nozzle is at a predetermined position;
- a position detector to detect, during and/or after an adjusting a plurality of adjustable bearings provided to the gantry wheel and that are interfacing with a support surface, when a projection from the proton beam nozzle is within a predetermined tolerance from both an axis of the gantry wheel and the isocenter; and
- a primary adjustment value determination unit to determine a primary adjustment value as a distance between the projection from the proton beam nozzle and the isocenter after adjustment at the predetermined position;
- wherein the rotation controller rotates the gantry wheel a predetermined number of degrees such that the interfacing adjustable bearings may be adjusted until the primary adjustment value is reached between the projection from the proton beam nozzle and the isocenter at each subsequent gantry wheel position; and
- wherein the rotation and adjustment are repeated until a full 360 degrees of rotation of the gantry wheel has been reached.

* * * * *